United States Patent
Li et al.

(10) Patent No.: US 9,630,957 B2
(45) Date of Patent: Apr. 25, 2017

(54) 2,3-BUTANEDIAMIDE EPOXIDE COMPOUND AND PREPARATION METHOD AND USE THEREOF

(71) Applicant: Institute of Pharmacology and Toxicology Academy of Military Medical Sciences P.L.A. China, Beijing (CN)

(72) Inventors: Song Li, Beijing (CN); Junhai Xiao, Beijing (CN); Xian Zhang, Beijing (CN); Wu Zhong, Beijing (CN); Zhibing Zheng, Beijing (CN); Lili Wang, Beijing (CN); Yunde Xie, Beijing (CN); Xingzhou Li, Beijing (CN); Xinbo Zhou, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 14/893,391

(22) PCT Filed: May 28, 2014

(86) PCT No.: PCT/CN2014/078581
§ 371 (c)(1),
(2) Date: Nov. 23, 2015

(87) PCT Pub. No.: WO2014/190899
PCT Pub. Date: Dec. 4, 2014

(65) Prior Publication Data
US 2016/0115160 A1     Apr. 28, 2016

(51) Int. Cl.
C07D 417/12   (2006.01)
C07D 303/48   (2006.01)
C07D 417/14   (2006.01)

(52) U.S. Cl.
CPC ......... *C07D 417/12* (2013.01); *C07D 303/48* (2013.01); *C07D 417/14* (2013.01)

(58) Field of Classification Search
CPC .......................... C07D 417/12; C07D 303/48
See application file for complete search history.

(56) References Cited

U.S. PATENT DOCUMENTS

| | | | |
|---|---|---|---|
| 4,387,238 A | 6/1983 | Goi et al. | |
| 4,849,531 A | 7/1989 | Häbich et al. | |
| 4,863,916 A | 9/1989 | Häbich et al. | |
| 2003/0158152 A1 | 8/2003 | Pecanha et al. | |
| 2014/0080840 A1 | 3/2014 | Li et al. | |
| 2014/0114068 A1 | 4/2014 | Jung et al. | |

FOREIGN PATENT DOCUMENTS

| | | | |
|---|---|---|---|
| CN | 1406223 A | 3/2003 | |
| CN | 102485717 A | 6/2012 | |
| CN | 102743387 A | 10/2012 | |
| CN | 102838523 A | 12/2012 | |
| EP | 0 921 122 A1 | 6/1999 | |
| JP | EP 0921122 A1 * | 6/1999 | ......... C07D 303/48 |
| WO | WO 02/42412 A2 | 5/2002 | |
| WO | WO 2012/173448 A2 | 12/2012 | |
| WO | WO 2013/049382 A2 | 4/2013 | |

OTHER PUBLICATIONS

Schafer et al. Drug Discovery Today, 2008, 13 (21/22), 913-916.*
Horig et al. Journal of Translational Medicine 2004, 2(44), p. 1-8.*
International Search Report (ISR) for PCT/CN2014/078581; I.A. fd: May 28, 2014, mailed Sep. 4, 2014, by the State Intellectual Property Office of the P.R. China, Beijing, China.
International Preliminary Report on Patentability (IPRP) including the Written Opinion of the International Searching Authority (PCT Rule 44*bis*) for PCT/CN2014/078581; I.A. fd: May 28, 2014, issued Dec. 1, 2015, by the International Bureau of WIPO, Geneva, Switzerland.
Miller, M. W., "Derivatives of (−)-trans-2,3-epoxysuccinic acid and some of their biological effects," J. Med. Chem., (May 1963), 6(3): 233-237, ACS Publications.
Moseley, JD, "Preparation of dicarboxylate analogues of cerulenin," J. Heterocyclic Chemistry, (Jul.-Aug. 2005), 42(5): 819-830.
Murata, M et al., "Novel epoxysuccinyl peptides. Selective inhibitors of cathepsin B, in vitro," FEBS Lett, (Mar. 1991); 280(2): 307-310.
Häbich, D et al., "Synthesis of an optically active 4-acetoxyazetidinone intermediate for penems and carbapenems," J. Heterocyclic Chemistry, (Mar. 1988), 25(2): 487-494.

(Continued)

*Primary Examiner* — Yong Chu
(74) *Attorney, Agent, or Firm* — Sterne, Kessler, Goldstein & Fox P.L.L.C.

(57) ABSTRACT

Provided are a compound of formula I which can be used as a drug against small RNA virus infections, and optical isomers, pharmaceutically acceptable salts, solvates or hydrates thereof. Also provided are the preparation method of the compound, the method for using the compound for treating bacterial infections and the use of the compound in the preparation of a drug for preventing and/or treating viral diseases caused by small RNA viruses.

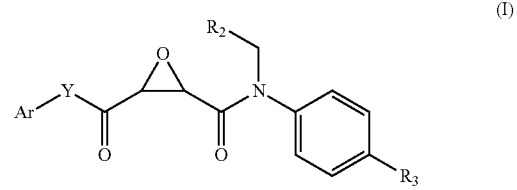

14 Claims, No Drawings

(56) References Cited

OTHER PUBLICATIONS

Extended European search report, including the supplemental European search report and the European search opinion, for EP Appl. No. 14804849.9, dated Sep. 26, 2016, European Patent Office, Munich, Germany.

"First Office Action" for CN Appl. No. 201310210954.0, dated issued Nov. 11, 2016, including "Search Report," The State Intellectual Property Office of People's Republic of China, Beijing, CN.

Wang, Hong-Jiang, Design, synthesis and evaluation of EV71 VP1 Inhibitors, Dissertation, Section 2.1.2.1, Dissertation pp. 21-24 (Dissertation database pp. E079-4) Dec. 2010, Shenyang Pharmaceutical University, Shenyang, China.

* cited by examiner

2,3-BUTANEDIAMIDE EPOXIDE COMPOUND AND PREPARATION METHOD AND USE THEREOF

TECHNICAL FIELD

The present invention relates to the field of pharmaceutical chemical engineering, especially to 2,3-epoxybutanediamide compounds which can be used as a drug against small RNA virus infections. The present invention also relates to the preparation method of the compounds, the method for using the compounds for treating bacterial infections and the use of the compounds in the preparation of a drug for preventing and/or treating viral diseases caused by small RNA viruses.

BACKGROUND ART

The enterovirus 71 (EV71) belongs to enterovirus genus of small ribosomal virus family. Since the first isolation of the virus in California in 1969, from North America, Europe, Australia to Asia, many outbreaks of EV71 are reported in succession worldwide. Over the past 20 years, the Asian-Pacific region suffers from EV71 seriously, which becomes the focus of health problems in some countries in the region. Infection of EV71 often causes slight symptom hand-foot-and-mouth disease (HFMD) in infants, however, it can be complicated with serious nervous system disease in some of the virus infected infants, such as aseptic meningitis, encephalitis and acute flaccid paralysis, or even death. For example, outbreak in Taiwan in 1998 causes 405 children cases in all have neurological complications, pneumonedema, pneumorrhagia and myocarditis, wherein 78 cases died. In 2008, HFMD cases are up to more than 6,000 cases in Fuyang city of Anhui province, wherein 24 children cases died, on May 2 in the same year, HFMD is included in category C statutory infectious diseases by the Ministry of Health to report and manage.

Over the past few decades, in order to eradicate poliomyelitis, the outbreak of epidemic diseases has been reduced greatly with progress obtained in efficient vaccine and public health undertakings. However, the emergence of EV71 poses a new threat to children, especially specific therapeutic drug and vaccine against such disease are absent currently. As to the serious cases resulted from EV71 infection, supporting treatment is still the main treatment method. Accordingly, it is an very urgent task to develop special antiviral drug against EV71 to protect children from harm resulted from EV71 virus infection.

EV71 belongs to picornaviridae, it is sense single strand RNA molecule containing about 7,400 nucleotides without capsule structure. In the early stage of infection, the viral particle binds to the receptors in host cells, and releases viral RNA into cytoplasm. Once the genome comes into the host cell, it uses viral RNA as the messenger RNA, which has its own internal ribosome entry site (IRES) and poly A tail, and is translated by cap independent mechanism, and encodes a polyprotein chain. After that, the polyprotein is cut into the mature viral functional protein under mediating by viral 2A protease and 3C protease. The viral RNA is not only the messenger RNA for translating protein, but also template required by the virus encoded RNA dependent RNA polymerase (RdRP, known as 3D) in the replication process. In the infected cell, the replication of viral RNA occurs in the tonoplast structure in cytoplasm. Different from 3D protein, 2C protein of virus is highly conservative among human enteric virus, and is deemed as a part of virus replication complex in tonoplast. After that, the offspring sense strand viral RNA is encapsulated by viral coat protein and is assembled into new infective virus particle. Finally, infection triggers apoptosis pathway by 2A protease and 3C protease, the host cell is lysed, and the new virus particles are released.

Maturation cleavage is key step in synthesis of EV71 protein. As to other human enteric viruses, 2A protease and 3C protease are important proteases in processing precursor polyprotein in virus.

The purpose of the present invention is to synthetize a new 3C protease inhibitor, for use in the preparation of a drug for preventing and/or treating viral diseases caused by small RNA viruses.

CONTENTS OF THE INVENTION

Summary of the Invention

The invention provides a compound of formula I and optical isomers, pharmaceutically acceptable salts, solvates or hydrates thereof,

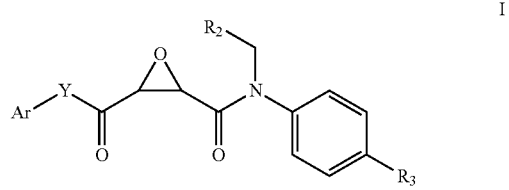

wherein,
Y is independently —O—, —S—, —C($R_4$)$_2$—, —N($R_4$)— or hydroxy, wherein when Y is hydroxy, Ar- is absent;

$R_4$ is independently hydrogen or $C_{1-6}$ alkyl;

Ar is independently cycloalkyl, heterocycloalkyl, aryl or heteroaryl, which is optionally and independently mono- or poly-substituted by 1, 2, 3, 4 or 5 $R_1$;

$R_1$ is independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl or nitro;

$R_2$ is independently hydrogen, halogen, aryl or heteroaryl, wherein said aryl or heteroaryl is optionally and independently mono- or poly-substituted by 1, 2, 3, 4 or 5 substituents, and the substituents are independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl or nitro;

$R_3$ is independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl, nitro or a group of formula

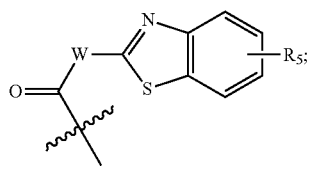

$R_5$ is independently hydrogen or $C_{1-6}$ alkyl;
W is independently —$C(R_6)_2$—, —$N(R_6)$—, —O— or —S—; and
$R_6$ is independently hydrogen or $C_{1-6}$ alkyl.

DETAILED DESCRIPTION OF THE INVENTION

Detailed description of each aspect and feature of the application is further illustrated as follows.

In the first aspect, the invention provides a compound of formula I and optical isomers, pharmaceutically acceptable salts, solvates or hydrates thereof,

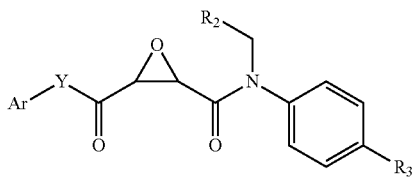

I wherein,
Y is independently —O—, —S—, —$C(R_4)_2$—, —$N(R_4)$— or hydroxy, wherein when Y is hydroxy, Ar- is absent;
$R_4$ is independently hydrogen or $C_{1-6}$ alkyl;
Ar is independently cycloalkyl, heterocycloalkyl, aryl or heteroaryl, which is optionally and independently mono- or poly-substituted by 1, 2, 3, 4 or 5 $R_1$;
$R_1$ is independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl or nitro;
$R_2$ is independently hydrogen, halogen, aryl or heteroaryl, wherein said aryl or heteroaryl is optionally and independently mono- or poly-substituted by 1, 2, 3, 4 or 5 substituents, and the substituents are independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl or nitro;
$R_3$ is independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl, nitro or a group of formula

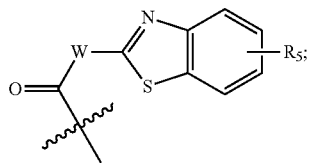

$R_5$ is independently hydrogen or $C_{1-6}$ alkyl;
W is independently —$C(R_6)_2$—, —$N(R_6)$—, —O— or —S—; and
$R_6$ is independently hydrogen or $C_{1-6}$ alkyl.

In one embodiment in the first aspect of the invention, Y is —$N(R_4)$—, wherein $R_4$ is independently hydrogen or $C_{1-6}$ alkyl, preferably hydrogen.

In another embodiment in the first aspect of the invention, Y is —O— or —S—.

In another embodiment in the first aspect of the invention, Y is —$C(R_4)_2$—, wherein $R_4$ is independently hydrogen or $C_{1-6}$ alkyl, preferably hydrogen.

In yet another embodiment in the first aspect of the invention, Y is hydroxy, and Ar is absent at present.

In yet another embodiment in the first aspect of the invention, Ar is aryl or heteroaryl, which is optionally and independently mono- or poly-substituted by 1, 2 or 3 $R_1$.

In yet another embodiment in the first aspect of the invention, Ar is aryl, preferably $C_{6-14}$ aryl, more preferably phenyl or naphthyl, most preferably phenyl, which is optionally and independently mono- or poly-substituted by 1, 2 or 3 $R_1$.

In another embodiment in the first aspect of the invention, Ar is heteroaryl, preferably 5- to 10-membered heteroaryl, more preferably oxazolyl, imidazolyl or thiazolyl, most preferably thiazolyl, which is optionally and independently mono- or poly-substituted by 1 or 2 $R_1$.

In one embodiment in the first aspect of the invention, $R_1$ is independently hydrogen, halogen, alkyl, alkoxy, hydroxy, cyano, amino, alkylamino, dialkylamino, hydroxyalkyl, haloalkyl, haloalkoxy, alkylthio, alkoxycarbonyl or nitro.

In another embodiment in the first aspect of the invention, $R_1$ is independently hydrogen, halogen, alkoxy, hydroxy, amino, alkylamino, dialkylamino, haloalkoxy, alkylthio, alkoxycarbonyl or nitro.

In another embodiment in the first aspect of the invention, $R_1$ is independently hydrogen, halogen, alkoxy, alkoxycarbonyl or nitro.

In one embodiment in the first aspect of the invention, $R_2$ is aryl or heteroaryl, which is optionally and independently mono- or poly-substituted by 1, 2 or 3 substituents, and the substituent is independently hydrogen, halogen, alkyl, alkoxy, hydroxy, amino, alkylamino, dialkylamino, haloalkyl, haloalkoxy or alkylthio, preferably hydrogen, halogen, alkyl, alkoxy, hydroxy or amino, more preferably hydrogen or halogen.

In another embodiment in the first aspect of the invention, $R_2$ is aryl, preferably $C_{6-14}$ aryl, more preferably phenyl or naphthyl, most preferably phenyl, which is optionally and independently mono- or poly-substituted by 1, 2 or 3 substituents, and the substituent is independently hydrogen, halogen, alkyl, alkoxy, hydroxy, amino, alkylamino, dialkylamino, haloalkyl, haloalkoxy or alkylthio, preferably hydrogen, halogen, alkyl, alkoxy, hydroxy or amino, more preferably hydrogen or halogen.

In another embodiment in the first aspect of the invention, $R_2$ is heteroaryl, preferably 5- to 10-membered heteroaryl, more preferably pyridyl, pyrimidyl or triazinyl, which is optionally and independently mono- or poly-substituted by 1 or 2 substituents, and the substituent is independently hydrogen, halogen, alkyl, alkoxy, hydroxy, amino, alkylamino, dialkylamino, haloalkyl, haloalkoxy or alkylthio, preferably hydrogen, halogen, alkyl, alkoxy, hydroxy or amino, more preferably hydrogen or halogen.

In one embodiment in the first aspect of the invention, $R_3$ is independently hydrogen, halogen, alkyl, alkoxy, hydroxy, cyano, amino, alkylamino, dialkylamino, alkylthio or a group of formula

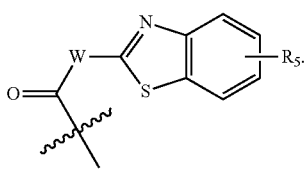

In another embodiment in the first aspect of the invention, $R_3$ is independently hydrogen or a group of formula

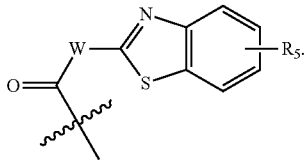

In one embodiment in the first aspect of the invention, $R_5$ is hydrogen.

In another embodiment in the first aspect of the invention, $R_5$ is $C_{1-6}$ alkyl.

In one embodiment in the first aspect of the invention, W is $—C(R_6)_2—$, wherein $R_6$ is independently hydrogen or $C_{1-6}$ alkyl, preferably hydrogen.

In another embodiment in the first aspect of the invention, W is $—N(R_6)—$, wherein $R_6$ is independently hydrogen or $C_{1-6}$ alkyl, preferably hydrogen.

In another embodiment in the first aspect of the invention, W is $—O—$ is $—S—$.

In the second aspect, the invention provides a pharmaceutical composition comprising a therapeutically and/or prophylactically effective amount of the compound of formula I in the first aspect of the invention, optical isomers, pharmaceutically acceptable salts, solvates or hydrates thereof, and optionally one or more pharmaceutically acceptable carriers or excipients.

In the third aspect, the invention provides the use of the compound of formula I in the first aspect of the invention, optical isomers, pharmaceutically acceptable salts, solvates or hydrates thereof, or the pharmaceutical composition in the second aspect of the invention in the preparation of a drug for treating and/or preventing diseases or conditions related to virus infections.

In one embodiment in the third aspect of the invention, the virus is small RNA virus.

In one embodiment in the third aspect of the invention, the small RNA virus is selected from the group consisting of rhinovirus, enterovirus, aphthovirus, cardiovirus, hepatovirus and parechovirus.

In one embodiment in the third aspect of the invention, the diseases or conditions related to virus infections are selected from the group consisting of respiratory diseases (including but not limited to: common cold (such as summer cold), pharyngitis, tonsillitis and croup), hand-foot-mouth disease, meningitis/cephalitis, acute poliomyelitis, cardiovascular diseases, hemorrhagic conjunctivitis, hepatitis, and so on.

In the fourth aspect, the invention provides the compound of formula I in the first aspect of the invention, optical isomers, pharmaceutically acceptable salts, solvates or hydrates thereof, or the pharmaceutical composition in the second aspect of the invention, which are used for treating the diseases or conditions related to virus infections.

In one embodiment in the fourth aspect of the invention, the virus is small RNA virus.

In one embodiment in the fourth aspect of the invention, the small RNA virus is selected from the group consisting of rhinovirus, enterovirus, aphthovirus, cardiovirus, hepatovirus and parechovirus.

In one embodiment in the fourth aspect of the invention, the diseases or conditions related to virus infections are selected from the group consisting of: respiratory diseases (including but not limited to: common cold (such as summer cold), pharyngitis, tonsillitis and croup), hand-foot-mouth disease, meningitis/cephalitis, acute poliomyelitis, cardiovascular diseases, hemorrhagic conjunctivitis, hepatitis, and so on.

In the fifth aspect, the invention provides a method for treating and/or preventing diseases or conditions related to virus infections in a subject comprising administering a therapeutically and/or prophylactically effective amount of at least one of the compound of formula I in the first aspect of the invention and optical isomers, pharmaceutically acceptable salts, solvates or hydrates thereof, or the pharmaceutical composition in the second aspect of the invention to the subject in need thereof.

In one embodiment in the fifth aspect of the invention, the virus is small RNA virus.

In one embodiment in the fifth aspect of the invention, the small RNA virus is selected from the group consisting of rhinovirus, enterovirus, aphthovirus, cardiovirus, hepatovirus and parechovirus.

In one embodiment in the fifth aspect of the invention, the diseases or conditions related to virus infections are selected from the group consisting of: respiratory diseases (including but not limited to: common cold (such as summer cold), pharyngitis, tonsillitis and croup), hand-foot-mouth disease, meningitis/cephalitis, acute poliomyelitis, cardiovascular diseases, hemorrhagic conjunctivitis, hepatitis, and so on.

In the sixth aspect, the invention provides a method for preparing the compound of formula I in the first aspect of the invention, and optical isomers, pharmaceutically acceptable salts, solvates or hydrates thereof.

The feature of any aspect or any sub-aspect of such aspect of the invention is also applicable to any other aspect or any sub-aspect of such other aspect of the invention. In the invention, for example, when referring to "the first aspect of the invention", "any aspect" indicates any sub-aspect of the first aspect of the invention, and when other aspects is referred to in similar way, they also have the same meaning.

All literatures cited in the invention, their entire contents are incorporated herein by reference, moreover, if the meanings expressed by these literatures are inconsistent with the invention, the expression in the invention prevails. In addition, each term and phrase used in the invention have the general meaning well known for the person skilled in the art, even so, the invention will still make further detailed illustration and explanation to these terms and phrases herein, and if the mentioned term and phrase are inconsistent with the common meaning, the meaning expressed in the invention prevails.

As used herein, the term "halogen" refers to fluorine, chlorine, bromine or iodine. Preferred halogen group is fluorine, chlorine or bromine.

As used herein, the term "alkyl" refers to a saturated linear or branched monovalent hydrocarbon group having 1 to 20 carbon atoms ($C_{1-20}$), preferably 1 to 12 carbon atoms ($C_{1-12}$), 1 to 6 carbon atoms ($C_{1-6}$), 1 to 4 carbon atoms ($C_{1-4}$) or 1 to 3 carbon atoms ($C_{1-3}$). Typical examples of "alkyl" include, but not limited to, methyl, ethyl, n-propyl, isopropyl, n-butyl, iso-butyl, t-butyl, n-pentyl, t-pentyl, neopentyl, hexyl, heptyl, octyl and the like.

As used herein, the term "alkenyl" refers to an olefinic unsaturated linear or branched monovalent hydrocarbon group containing at least one carbon-carbon double bond (—C═C—), which has 2 to 20 carbon atoms, preferably 2 to 12, 2 to 6, 2 to 4 or 2 to 3 carbon atoms. The typical examples of "alkenyl" include, but not limited to vinyl, propenyl, allyl, buten-1-yl, buten-2-yl, penten-1-yl, penten-2-yl, 1,3-pentadienyl, hexen-1-yl, hexen-2-yl, 1,3-hexadienyl, heptenyl, octenyl and the like.

As used herein, the term "alkynyl" refers to an acetylenic unsaturated linear or branched monovalent hydrocarbon group containing at least one carbon-carbon triple bond (—C≡C—), which has 2 to 20 carbon atoms, preferably 2 to 12, 2 to 6, 2 to 4 or 2 to 3 carbon atoms. The typical examples of "alkynyl" include, but not limited to ethynyl, propynyl, propargyl, butynyl, pentynyl, hexynyl, heptynyl, octynyl and the like.

As used herein, the term "cycloalkyl" refers to a saturated cyclic hydrocarbon group having 3 to 16 carbon atoms, preferably 3 to 12, 3 to 8, 5 to 8, 3 to 6 or 5 to 6 carbon atoms, and having monocyclic ring or bicyclic ring or multiple fused rings (including fused ring system and bridged ring system). The typical examples of "cycloalkyl" include, but not limited to, mono ring structures such as cyclopropyl, cyclobutyl, cyclopentyl, cyclohexyl, cycloheptyl, cyclooctyl, 1-methyl-cyclopropyl, 2-methyl-cyclopentyl, 2-methylcyclooctyl and the like; and bicyclic structures such as bicyclo[2,2,1]heptyl; and polycyclic structures such as adamantyl and the like.

As used herein, the term "heterocycloalkyl" refers to cyloalkyl as defined herein containing one or two or more heteroatoms which are independently selected from the group consisting of N, O and S. The typical examples of "heterocycloalkyl" include, but not limited to, tetrahydrofuranyl, tetrahydrothienyl, pyrrolidinyl, piperazinyl, thiazinyl, piperidinyl, morpholinyl and the like.

As used herein, the term "alkoxy" refers to group —$OR_{11}$, wherein $R_{11}$ is alkyl or cycloalkyl as defined herein. The typical examples of "alkoxy" include, but not limited to, methoxy, ethoxy, n-propoxy, iso-propoxy, n-butoxy, t-butoxy, sec-butoxy, n-pentyloxy, n-hexyloxy, 1,2-dimethylbutoxy, cyclohexyloxy, cyclopropyloxy and the like.

As used herein, the term "hydroxy" refers to —OH.

As used herein, the term "cyano" refers to —CN.

As used herein, the term "amino" refers to —$NH_2$.

As used herein, the term "nitro" refers to —$NO_2$.

As used herein, the term "alkoxycarbonyl" refers to —C(O)—O—$R_{11}$, wherein $R_{11}$ is selected from the group consisting of alkyl and cycloalkyl as defined herein. The typical examples of "alkoxycarbonyl" include, but not limited to, methoxycarbonyl, ethoxycarbonyl, propoxycarbonyl, butoxycarbonyl and the like.

As used herein, the term "alkylamino" refers to group —$NHR_{11}$, wherein $R_{11}$ is selected from the group consisting of alkyl and cycloalkyl as defined herein. The typical examples of "alkylamino" include, but not limited to, methylamino, ethylamino, propylamino, butylamino, cyclopropylamino and the like.

As used herein, the term "dialkylamino" refers to group —$NR_{11}R_{12}$, wherein $R_{11}$ and $R_{12}$ is each independently selected from the group consisting of alkyl and cycloalkyl as defined herein. The typical examples of "dialkylamino" include, but not limited to dimethylamino, diethylamino, dipropylamino, dibutylamino and the like.

As used herein, the term "cyanoalkyl" refers to alkyl as defined herein mono- or poly-substituted by cyano. Preferred cyanoalkyl is cyanomethyl, cyanoethyl, cyanopropyl, cyanobutyl and the like.

As used herein, the term "hydroxyalkyl" refers to alkyl as defined herein mono- or poly-substituted by hydroxy. Preferred hydroxyalkyl is hydroxymethyl, hydroxyethyl, hydroxypropyl, hydroxybutyl and the like.

As used herein, the term "haloalkyl" refers to alkyl as defined herein mono- or poly-substituted by halogen such as fluorine, chlorine, bromine or iodine. Preferred haloalkyl is chloromethyl, chloroethyl, dichloroethyl, bromoethyl, trifluoromethyl, difluoromethyl, fluoromethyl, iodomethyl and the like.

As used herein, the term "haloalkoxy" refers to alkoxy as defined herein mono- or poly-substituted by halogen such as fluorine, chlorine, bromine or iodine. Preferred haloalkoxy is chloromethoxy, chloroethoxy, dichloroethoxy, bromoethoxy, trifluoromethoxy, difluoromethoxy, monofluoromethoxy and the like.

As used herein, the term "alkylthio" refers to group wherein $R_{11}$ is alkyl or cycloalkyl as defined herein. The typical examples of "alkylthio" include, but not limited to, methylthio, ethylthio, propylthio, butylthio, cyclohexylthio and the like.

As used herein, the term "aryl" refers to an unsaturated aromatic carbocyclic group having 6-14 carbon atoms ($C_{6-14}$) and having a single ring or two or more fused rings. The aryl preferably has 6-10 ($C_{6-10}$) or 6 carbon atoms ($C_6$). The typical examples of the "aryl" include, but not limited to, phenyl, naphthyl and anthryl and the like, preferably phenyl and naphthyl, more preferably phenyl.

As used herein, the term "heteroaryl" refers to an aromatic ring group having 5-14 ring members, wherein one or two or more carbon atoms are replaced by heteroatoms independently selected from the group consisting of O, S or N. "Heteroaryl" includes monocyclic heteroaryl and polycyclic heteroaryl. As used herein, the term "heteroaryl" also includes groups in which aromatic ring is fused with one or more non-aromatic rings (carbocyclic rings or heterocyclic rings), wherein the linking group or point is located on the aromatic ring or the non-aromatic ring. The heteroaryl preferably has 5-10 ring members, more preferably 5-6 ring members. The typical examples of "heteroaryl" include, but not limited to, pyridyl, pyrimidyl, triazolyl, thiazolyl, oxazolyl, imidazolyl, furyl, indolyl, quinolyl, isoquinolyl, quinazolinyl, quinoxalinyl and the like.

The above groups defined by each term can be optionally mono- or poly-substituted by —CN, —OH, —$NH_2$, $C_{14}$ alkyl, $C_{14}$ alkylamino, $C_{14}$ alkoxy or halogen.

When the compound name used herein is inconsistent with the chemical structural formula, the chemical structural formula prevails.

As used herein, the term "pharmaceutically acceptable", when describing for example "pharmaceutically acceptable salt", not only means that the salt is physiologically acceptable in a subject, but also means that it is synthetic substance which has value in use pharmaceutically.

As used herein, the term "effective amount" refers to the dosage which realizes the treatment and/or prevention of the diseases or conditions of the invention in a subject.

As used herein, the term "pharmaceutical composition", which can also indicate "composition", can be used to realize the treatment and/or prevention of the diseases or conditions of the invention in a subject, especially in mammal.

As used herein, the term "subject" may refer to the patients or other animals which accept the compound of formula I or the pharmaceutical composition thereof to treat and/or prevent the diseases or conditions of the invention, especially mammal, such as human, dog, monkey, cattle, horse and so on.

As used herein, unless specifically indicated, "%" refers to the percentage of weight/weight, especially in the description of solid substance. Of course, when describing the liquid substance, the "%" can refer to the percentage of weight/volume (where the solid is dissolved in liquid), or can refer to the percentage of volume/volume (where the liquid is dispersed in liquid).

According to the invention, the compound represented by formula I in the first aspect of the invention or racemates, optical isomers, pharmaceutically acceptable salts, solvates or hydrates thereof are selected from the group consisting of:

(2S,3S)—$N^2$-benzyl-$N^2$-phenyl-$N^3$-(3,4-dimethoxyphenyl)-2,3-epoxybutanediamide (Compound 1);

(2S,3S)—$N^2$-benzyl-$N^2$-phenyl-$N^3$-(2-thiazolyl)-2,3-epoxybutanediamide (Compound 2);

(2S,3S)—$N^2$-benzyl-$N^2$-phenyl-$N^3$-(3,4-dichlorophenyl)-2,3-epoxybutanediamide (Compound 3);

(2S,3S)—$N^2$-benzyl-$N^2$-phenyl-$N^3$-(3-fluorophenyl)-2,3-epoxybutanediamide (Compound 4);

(2S,3S)—$N^2$-benzyl-$N^2$-phenyl-$N^3$-(4-fluorophenyl)-2,3-epoxybutanediamide (Compound 5);

(2S,3S)—$N^2$-benzyl-$N^2$-phenyl-$N^3$-(2-fluorophenyl)-2,3-epoxybutanediamide (Compound 6);

(2S,3S)—$N^2$-benzyl-$N^2$-phenyl-$N^3$-(3-methoxyphenyl)-2,3-epoxybutanediamide (Compound 7);

(2S,3S)—$N^2$-benzyl-$N^2$-phenyl-$N^3$-(3-chlorophenyl)-2,3-epoxybutanediamide (Compound 8);

(2S,3S)—$N^2$-benzyl-$N^2$-phenyl-$N^3$-(4-nitrophenyl)-2,3-epoxybutanediamide (Compound 9);

(2S,3S)—$N^2$-benzyl-$N^2$-phenyl-$N^3$-(2,3-dichlorophenyl)-2,3-epoxybutanediamide (Compound 10);

(2S,3S)—$N^2$-benzyl-$N^2$-phenyl-$N^3$-(2-chlorophenyl)-2,3-epoxybutanediamide (Compound 11);

(2S,3S)—$N^2$-benzyl-$N^2$-phenyl-$N^3$-(4-chlorophenyl)-2,3-epoxybutanediamide (Compound 12);

(2S,3S)—$N^2$-benzyl-$N^2$-phenyl-$N^3$-(2-methyl-3-chlorophenyl)-2,3-epoxybutanediamide (Compound 13);

(2S,3S)—$N^2$-benzyl-$N^2$-phenyl-$N^3$-(3-bromophenyl)-2,3-epoxybutanediamide (Compound 14);

(2S,3S)—$N^2$-benzyl-$N^2$-phenyl-$N^3$-(2-bromophenyl)-2,3-epoxybutanediamide (Compound 15);

(2S,3S)-3-((4-(benzo[d]thiazol-2-ylcarbamoyl)phenyl)(4-fluorobenzyl)carbamoyl)oxirane-2-carboxylic acid (Compound 16);

(2S,3S)—$N^2$-(4-(benzo[d]thiazol-2-ylcarbamoyl)phenyl)-$N^3$-(3,4-dimethoxyphenyl)-$N^2$-(4-fluorobenzyl)-2,3-epoxybutanediamide (Compound 17);

(2S,3S)—$N^2$-(4-(benzo[d]thiazol-2-ylcarbamoyl)phenyl)-$N^3$-(3-bromophenyl)-$N^2$-(4-fluorobenzyl)-2,3-epoxybutanediamide (Compound 18);

(2S,3S)—$N^2$-(4-(benzo[d]thiazol-2-ylcarbamoyl)phenyl)-$N^3$-(4-chlorophenyl)-$N^2$-(4-fluorobenzyl)-2,3-epoxybutanediamide (Compound 19);

(2S,3S)—$N^2$-(4-(benzo[d]thiazol-2-ylcarbamoyl)phenyl)-$N^3$-(4-methoxyphenyl)-$N^2$-(4-fluorobenzyl)-2,3-epoxybutanediamide (Compound 20);

(2S,3S)—$N^2$-(4-(benzo[d]thiazol-2-ylcarbamoyl)phenyl)-$N^3$-(3-methoxyphenyl)-$N^2$-(4-fluorobenzyl)-2,3-epoxybutanediamide (Compound 21);

(2S,3S)—$N^2$-(4-(benzo[d]thiazol-2-ylcarbamoyl)phenyl)-$N^3$-(3,4-difluorophenyl)-$N^2$-(4-fluorobenzyl)-2,3-epoxybutanediamide (Compound 22);

(2S,3S)—$N^2$-(4-(benzo[d]thiazol-2-ylcarbamoyl)phenyl)-$N^3$-(3-chlorophenyl)-$N^2$-(4-fluorobenzyl)-2,3-epoxybutanediamide (Compound 23);

(2S,3S)—$N^2$-(4-(benzo[d]thiazol-2-ylcarbamoyl)phenyl)-$N^3$-(4-nitrophenyl)-$N^2$-(4-fluorobenzyl)-2,3-epoxybutanediamide (Compound 24);

(2S,3S)—$N^2$-(4-(benzo[d]thiazol-2-ylcarbamoyl)phenyl)-$N^3$-(2,3-dichlorophenyl)-$N^2$-(4-fluorobenzyl)-2,3-epoxybutanediamide (Compound 25);

(2S,3S)—$N^2$-(4-(benzo[d]thiazol-2-ylcarbamoyl)phenyl)-$N^3$-(2,4-dichlorophenyl)-$N^2$-(4-fluorobenzyl)-2,3-epoxybutanediamide (Compound 26);

(2S,3S)—$N^2$-(4-(benzo[d]thiazol-2-ylcarbamoyl)phenyl)-$N^3$-(2-bromophenyl)-$N^2$-(4-fluorobenzyl)-2,3-epoxybutanediamide (Compound 27);

(2S,3S)—$N^2$-(4-(benzo[d]thiazol-2-ylcarbamoyl)phenyl)-$N^3$-(2-methyl-3-chlorophenyl)-$N^2$-(4-fluorobenzyl)-2,3-epoxybutanediamide (Compound 28);

(2S,3S)—$N^2$-(4-(benzo[d]thiazol-2-ylcarbamoyl)phenyl)-$N^3$-(4-fluorophenyl)-$N^2$-(4-fluorobenzyl)-2,3-epoxybutanediamide (Compound 29);

(2S,3S)—$N^2$-(4-(benzo[d]thiazol-2-ylcarbamoyl)phenyl)-$N^3$-(3-fluorophenyl)-$N^2$-(4-fluorobenzyl)-2,3-epoxybutanediamide (Compound 30);

(2S,3S)—$N^2$-(4-(benzo[d]thiazol-2-ylcarbamoyl)phenyl)-$N^3$-(3,4-dichlorophenyl)-$N^2$-(4-fluorobenzyl)-2,3-epoxybutanediamide (Compound 31);

(2S,3S)—$N^2$-(4-(benzo[d]thiazol-2-ylcarbamoyl)phenyl)-$N^2$-(4-fluorobenzyl)-$N^3$-(2-thiazolyl)-2,3-epoxybutanediamide (Compound 32);

(2S,3S)—$N^2$-(4-(benzo[d]thiazol-2-ylcarbamoyl)phenyl)-$N^2$-(4-fluorobenzyl)-$N^3$-(4-ethoxycarbonylthiazol-2-yl)-2,3-epoxybutanediamide (Compound 33);

(2S,3S)—$N^2$-(4-(benzo[d]thiazol-2-ylcarbamoyl)phenyl)-$N^2$-(4-fluorobenzyl)-$N^3$-(4-methoxycarbonylthiazol-2-yl)-2,3-epoxybutanediamide (Compound 34);

(2S,3S)—$N^2$-(4-(benzo[d]thiazol-2-ylcarbamoyl)phenyl)-$N^2$-(4-fluorobenzyl)-$N^3$-(5-ethoxycarbonylthiazol-2-yl)-2,3-epoxybutanediamide (Compound 35);

(2S,3S)—$N^2$-(4-(benzo[d]thiazol-2-ylcarbamoyl)phenyl)-$N^2$-(4-fluorobenzyl)-$N^3$-(5-methoxycarbonylthiazol-2-yl)-2,3-epoxybutanediamide (Compound 36);

(2S,3S)—$N^2$-(4-(benzo[d]thiazol-2-ylcarbamoyl)phenyl)-$N^3$-(2-methoxyphenyl)-$N^2$-(4-fluorobenzyl)-2,3-epoxybutanediamide (Compound 37);

(2S,3S)-3-((4-(benzo[d]thiazol-2-ylcarbamoyl)phenyl)(benzyl)carbamoyl)oxirane-2-carboxylic acid (Compound 38);

(2S,3S)—$N^2$-(4-(benzo[d]thiazol-2-ylcarbamoyl)phenyl)-$N^2$-benzyl-$N^3$-(3,4-dimethoxyphenyl)-2,3-epoxybutanediamide (Compound 39);

(2S,3S)—$N^2$-(4-(benzo[d]thiazol-2-ylcarbamoyl)phenyl)-$N^2$-benzyl-$N^3$-(3,4-dichlorophenyl)-2,3-epoxybutanediamide (Compound 40);

(2S,3S)—$N^2$-(4-(benzo[d]thiazol-2-ylcarbamoyl)phenyl)-$N^2$-benzyl-$N^3$-(4-methoxy carbonylthiazol-2-yl)-2,3-epoxybutanediamide (Compound 41);

(2S,3S)—$N^2$-(4-(benzo[d]thiazol-2-ylcarbamoyl)phenyl)-$N^2$-benzyl-$N^3$-(5-methoxy carbonylthiazol-2-yl)-2,3-epoxybutanediamide (Compound 42);

$N^2$-benzyl-$N^2$-phenyl-$N^3$-(3-bromophenyl)-2,3-epoxybutanediamide (Compound 43).

According to the invention, the compound of the invention can be illustratively prepared through the following reaction route:

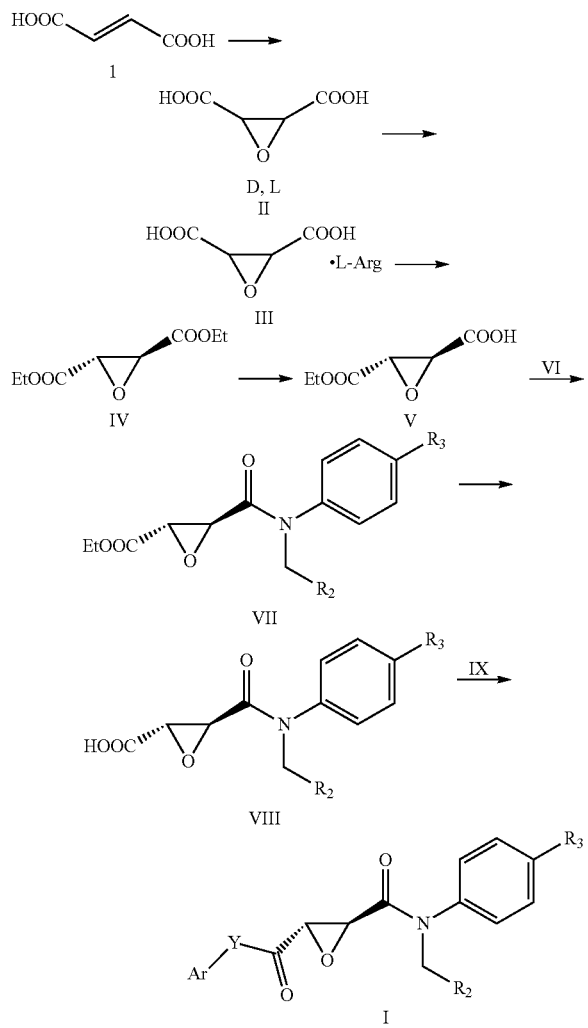

For example, the fumaric acid is used as starting material, and a pair of racemates are generated by cyclization with $H_2O_2$, and the compound of formula II, i.e., epoxybutanedioic acid, is obtained. The salt forming reaction is carried out between the compound of formula II and L-Arginine (L-Arg), and the compound of formula III is obtained. The compound of formula III is subjected to chiral resolution, and the single enantiomer of the compound of formula III is obtained. The esterification reaction of single enantiomer and ethanol is carried out in the presence of the catalyst concentrated sulfuric acid, and the compound of formula IV is obtained. The compound of formula IV is subjected to esterolysis under catalysis of KOH, and the compound of formula V is obtained. The compound of formula VII can be produced from the compound of formula V in two ways. The compound of formula VII can be obtained from the compound of formula V and the compound of formula VI (such as, benzylaniline or (4-fluorobenzyl)aniline) using HATU as the condensation agent, wherein $R_2$ and $R_3$ in formula VII are defined as in the above formula I. However, the condensation of the compound of formula V and another compound of formula VI (such as, N-(benzo[d]thiazol-2-yl)-4-(4-fluorobenzylamino)benzamide or N-(benzo[d]thiazol-2-yl)-4-(benzylamino)benzamide) cannot be achieved by using the above condensation agent. Thus, the compound of formula V can firstly react with oxalyl chloride under the ice bath to prepare the corresponding acyl chloride, and the acyl chloride is further subjected to condensation reaction with the above compound of formula VI (N-(benzo[d]thiazol-2-yl)-4-(4-fluorobenzylamino)benzamide or N-(benzo[d]thiazol-2-yl)-4-(benzylamino)benzamide) to produce the compound of formula VII, wherein $R_2$ and $R_3$ in formula VII are defined as in the above formula I. The compound of formula VII is subjected to esterolysis under the catalysis of KOH, and the compound of formula VIII is obtained. The compound of formula VIII is then subjected to condensation reaction with the compound of formula IX in the presence of condensation agent HATU to produce the compound of formula I, wherein Ar and Y are defined as in above formula I. Wherein, the compound of formula IX is cycloalkylamine, arylamine or heteroarylamine. The compound of formula VI (such as, N-(benzo[d]thiazol-2-yl)-4-(4-fluorobenzylamino)benzamide or N-(benzo[d]thiazol-2-yl)-4-(benzylamino)benzamide) can be illustratively prepared through the following reaction route:

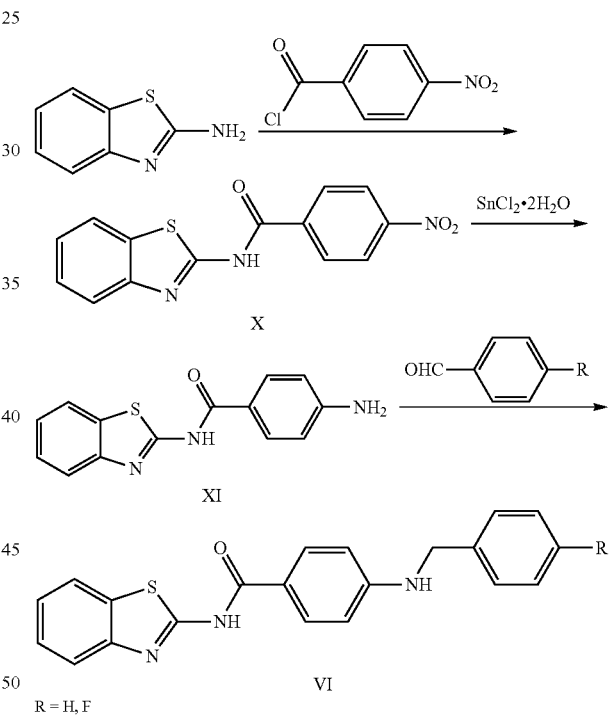

R = H, F

For example, 2-aminobenzothiazole and 4-nitrobenzoyl chloride produce the compound of formula X via nucleophilic substitution. The compound of formula X is reduced by stannous chloride dihydrate, and the compound of formula XI is obtained. The compound of formula XI reacts with 4-fluorobenzaldehyde or benzaldehyde, sodium cyanoborohydride in the presence of a strong dehydrant such as tetraisopropyl titanate to produce the compound of formula VI (such as, N-(benzo[d]thiazol-2-yl)-4-(4-fluorobenzylamino)benzamide or N-(benzo[d]thiazol-2-yl)-4-(benzylamino)benzamide).

As used herein, the term "pharmaceutically acceptable salt" includes the salt of an acid formed by the compound of the invention with the pharmaceutically acceptable inorganic acid or organic acid, or the salt of a base formed with the pharmaceutically acceptable base, wherein the salts of an acid includes, but not limited to, hydrochloride, hydrobromide, hydroiodide, nitrate, sulfate, bisulfate, phosphate, hydrogen phosphate, acetate, propionate, butyrate, oxalate, trimethylacetate, adipate, alginate, lactate, citrate, tartrate, succinate, malate, fumarate, picrate, aspartate, gluconate, benzoate, gluconate, esylate, besylate, tosylate and pamoate; the salts of a base include, but not limited to, ammonium salt, alkali metal salt such as sodium salt and potassium salt, alkaline-earth metal salts such as calcium salt and magnesium salt, organic base salt such as dicyclohexylamine salt and N-methyl-D-glucamine salt, and amino acid salt such as arginine salt and lysine salt.

According to the invention, the pharmaceutical composition comprises effective amount of the compound of formula I of the invention or the pharmaceutically acceptable salts or hydrates thereof and one or more appropriate pharmaceutically acceptable carriers. Herein, the pharmaceutically acceptable carriers include, but not limited to, ion exchanger, alumina, aluminum stearate, lecithin, serum protein such as human serum albumin, buffer agent such as phosphate, glycerin, sorbic acid, potassium sorbate, partial glyceride mixtures of saturated vegetable fatty acids, water, salt or electrolyte such as protamine sulfate, disodium hydrogen phosphate, potassium hydrogen phosphate, sodium chloride, zinc salt, colloidal silica, magnesium trisilicate, polyvinylpyrrolidone, cellulose-based substances, polyethylene glycol, sodium carboxymethylcellulose, polyacrylates, beeswax, polymer of polyoxyethylene and polyoxypropylene and lanolin.

The compound of the invention is a kind of superactive small RNA virus inhibitor, the prominent feature of such compound is that it can both prevent and treat the disease caused by small RNA virus. The diseases caused by small RNA virus include, but not limited to, respiratory diseases, hand-foot-mouth disease, meningitis/cephalitis, acute poliomyelitis, cardiovascular diseases, hemorrhagic conjunctivitis, hepatitis, and so on.

The respiratory diseases include, but not limited to, common cold (such as summer cold), pharyngitis, tonsillitis and croup. Such pathologies are generally caused by rhinovirus in small RNA virus family.

According to the invention, the pharmaceutical composition of the compound of the invention may be administered in any of the following modes: orally, inhalation by spraying, rectally, nasally, buccally, vaginally, topically, parenterally, such as subcutaneous, intravenous, intramuscular, intraperitoneal, intrathecal, intraventricular, intrasternal and intracranial injection or infusion, or by the aid of an explant reservoir. Among them, the oral, intraperitoneal or intravenous administration mode is preferred. In addition, in order to effectively treat neurological disorder in nerve centre, the compound of the invention may be administered by intraventricular to get over the possible low blood-brain barrier transmittance of the compound.

When administered orally, the compound of the present invention can be made into any orally acceptable preparation form, including, but not limited to, tablets, capsules, aqueous solutions or suspensions. Wherein, the carriers used in tablets generally include lactose and corn starch, and additionally, a lubricant such as magnesium stearate can also be added. Diluent used in capsules generally includes lactose and dried corn starch. Aqueous suspension is generally used by mixing active ingredient with a suitable emulsifier and suspending agent. If necessary, in the above oral preparations, certain sweetening agent, flavoring agent or coloring agent can also be added.

When administered rectally, the compound of the invention can be prepared into the form of suppository, which is obtained by mixing the drug with an appropriate non-irritating excipient. The excipient appears solid state at room temperature, and melts and releases the drug at the rectum temperature. Such excipient includes butter cacao, beewax and polyethylene glycol.

When administered topically, especially in the case of treating affected surface or organ where topical application easily reaches, such as ocular, dermal or lower intestinal nervous disorders, the compound of the present invention can be made into different topical preparation forms according to different affected surfaces or organs, as described below:

In the case of topical ocular administration, the compound of the present invention can be formulated into the preparation form of a micronised suspension or solution, wherein the carrier used is an isotonic sterile saline of a certain pH, in which a preservative, such as benzyl chloride alkoxide, may be added or not. In addition, for ocular administration, the compound can also be made into an ointment form such as vaseline ointment.

When topically administered to skin, the compound of the present invention can be made into suitable ointment, lotion or cream preparation form, wherein active ingredient is suspended or dissolved in one or more carriers. The carriers which can be used in ointment preparation include, but not limited to: mineral oil, liquid petrolatum, white petrolatum, propylene glycol, polyoxyethylene, polyoxypropylene, emulsifying wax and water; the carriers which can be used in lotion or cream include, but not limited to: mineral oil, dehydrated sorbitan monostearate, Tween 60, cetyl alkyl esters wax, hexadecene aryl alcohol, 2-octyldodecanol, benzyl alcohol and water.

When topically administered to lower intestine, the compound of the invention can be prepared into the rectal suppository preparation or suitable enema preparation form as stated above, additionally, the local transdermal patch can also be used.

The compound of the present invention can also be administered in the form of sterile injectable preparation, including sterile injectable aqueous or oily suspension or sterile injectable solution. Wherein, the carrier and solvent used include water, Ringer's solution and isotonic sodium chloride solution. Further, sterile nonvolatile oil can also be used as the solvent or suspending medium, for example, mono- or di-glycerides.

Also to be noted is that the particular dose and use method of the compound of the present invention depend on many factors including the patient's age, weight, gender, natural health status, nutritional status, the active intensity of the compound, the time of taking, the metabolic rate, the severity of the disease and the physician's subjective judgment. The preferred dose is between 0.01 and 100 mg/kg body weight/day.

MODE OF CARRYING OUT THE INVENTION

The present invention is further described by using Examples below. However, the scope of the invention is not limited to the following examples. The person skilled in the art can understand that, various changes and modifications can be made to the invention without departing from the spirit and scope of the invention. The invention makes general and/or specific description about the materials and experiment methods used in the experiments. Although many materials and operation methods used for realizing the purpose of the invention are well known in the art, herein the invention still makes detailed description as much as possible.

As for all the following Examples, the standard operations and purification methods known by the person skilled in the art can be used. Unless otherwise specified, all temperatures are expressed by ° C. (centigrade). The structure of a compound is determined by nuclear magnetic resonance (NMR) or mass spectrum (MS). The melting point (m.p.) of a compound is determined by RY-1 type Melting Point Apparatus, and the thermometer is not calibrated, and m.p. is expressed by ° C. $^1$H NMR is determined by Japan Electronics JNM-ECA-400 type NMR spectrometer. Mass spectrum is determined by API3000 (ESI) type mass spectrometer. All reaction solvents are subjected to standardized pretreatment unless specified.

Example 1

Synthesis of (2S,3S)—N$^2$-benzyl-N$^2$-phenyl-N$^3$-(3,4-dimethoxyphenyl)-2,3-epoxybutanediamide (Compound 1)

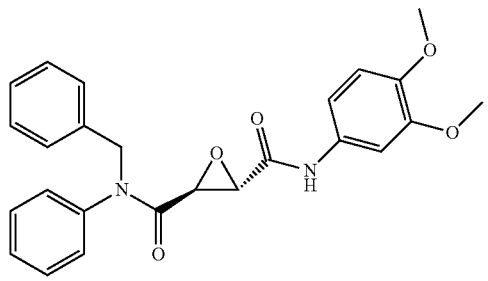 [SMILES: COc1ccc(NC(=O)[C@H]2O[C@@H]2C(=O)N(Cc2ccccc2)c2ccccc2)cc1OC]

Step 1.1 Synthesis of (2,3)-epoxybutanedioic acid

In the three-necked flask, the motor stirrer, thermometer and condenser pipe are provided respectively. Trans-butenedioic acid (174 g, 1.5 mol) and 450 ml of distilled water are added. And then a solution of NaOH (90 g, 2.25 mol) and 150 ml of water is added. The neutralization reaction raises the system temperature up to 70° C. Na$_2$WO$_4$ (49.5 g, 0.15 mol) and 30% H$_2$O$_2$ (204 ml, 1.8 mol) are added while the reaction system is hot, and the system temperature is maintained at 63-65° C. for about 20 minutes until the heat release is complete, and the system temperature tends to be stable. The pH is maintained at >4 during this period. The reaction is carried out at 63-65° C. for 3 hours, and the temperature is raised up to 75-80° C. for 1 hour. The condenser pipe is replaced with a constant pressure dropping funnel, and NaOH solution is added dropwise (20 g NaOH is dissolved in 100 ml of water). pH value is adjusted to 13-14, and starch-KI test paper appears no color, and the reaction is kept at 75-80° C. for 1 hour. Stop heating and concentrate under reduced pressure at 65° C. to a volume of 100 ml, and massive white viscous materials is precipitated. 500 ml of acetone is added, and the reaction is mechanically agitated for 1 hour and standing overnight. The reaction is suction filtered the next day, and the filter cake is washed twice with acetone and dried, yielding 360.4 g sodium salt.

The sodium salt (360.4 g) is heated and dissolved in 800 ml of water. The sodium salt solution is poured into an equimolar hot (about 50° C.) BaCl$_2$ (486 g/1500 ml water) solution, mechanically agitated for 12 hours at room temperature. Pumping filtration is carried out to collect the produced 476.9 g of barium salt.

The obtained barium salt (108 g) is suspended in 500 ml of diethyl ether, and 5 ml of water is added, and the reaction is cooled to 0-5° C. Under constant temperature and vigorous mechanically stirring, a mixed liquid of 37 g of concentrated sulfuric acid and 100 ml of diethyl ether is slowly added, and addition is completed after about 1 hour. Then the stirring is continued for 1 hour at the temperature of 5-10° C., and the reaction is warmed to the room temperature and stirred overnight. The formed BaSO$_4$ precipitate is removed by suction filtration. The filtrate is dried with anhydrous NaSO$_4$ and concentrated under reduced pressure to a volume of about 200 ml. The residue is diluted with two volumes of light petroleum ether (30-60° C.), generating a large quantity of solid. The solid is suction filtered and washed with light petroleum ether to give (2,3)-epoxybutanedioic acid. BaSO$_4$ in the previous step is extracted with 500 ml of diethyl ether, and the extract is treated as described above to obtain another portion of (2,3)-epoxybutanedioic acid, 45 g in total, and the yield is 45%. m.p. 207-209° C.

Step 1.2 Chiral resolution of (2,3)-epoxybutanedioic acid

The (2,3)-epoxybutanedioic acid (70.6 g, 0.535 mol) is dissolved into 2 L eggplant-shaped flask containing 1 L methanol. In 300 ml water, 93 g (0.535 mol) L-arginine is added, and heated to dissolve, and then added dropwise to the solution of (2,3)-epoxybutanedioic acid in methanol while stirring, and finally a large quantity of insoluble substance appears. After addition, the mixture is stirred at room temperature overnight. Precipitate is obtained by suction filtration, and rinsed with methanol-water (4:1) solution to give crude (2S,3S)-epoxybutanedioic acid L-arginine salt. The crude product is recrystallized (recrystallization conditions: 35 g crude product, water:methanol=130 ml/110 ml) after cooled to room temperature, crystallization is performed by cooling in a refrigerator to give pure product 24.2 g. $[\alpha]_D^{25}$=54.0 (c=1.00, H$_2$O), yield 31%, m.p. 171-173° C.

Step 1.3 Synthesis of (2S,3S)-epoxybutanedioic acid diethyl ester

At room temperature, the (2S,3S)-epoxybutanedioic acid L-arginine salt (45.3 g, 0.148 mol) is added to a 450 ml ethanol solution contained in 2 L three-necked flask and is suspended therein. The upper opening of the flask is equipped with a condenser, a drying tube and a constant pressure dropping funnel. The concentrated sulfuric acid (24 ml, 0.444 mol) is added dropwise with stirring. After addition, the solution is refluxed at 70° C. for 4.5 hours. After completion of the reaction, the reaction solution is concentrated, then diluted with 450 ml ice water, extracted with ethyl acetate (450 ml*3). The organic phase is washed with saturated NaHCO$_3$ (450 ml*2), then with saturated brine (450 ml*2), and dried with NaSO$_4$. Suction filtered, the filtrate is concentrated to give a yellow oily substance. After column chromatography, gradient elution: the columns are rinsed by petroleum ether, petroleum ether/ethyl acetate=20:

1, giving a colorless oily substance (2S,3S)-epoxybutanedioic acid diethyl ester, 22 g in total, and the yield is 79%.

Step 1.4 Synthesis of (2S,3S)-epoxybutanedioic acid monoethyl ester

The KOH (0.45 g, 8 mmol) is added to 4.5 ml of ethanol, stirred and heated to dissolve. The (2S,3S)-epoxybutanedioic acid diethyl ester (1.25 g, 6.7 mmol) is added to 10 ml of ethanol and stirred, and the temperature is controlled to 4-6° C. by ice bath, then a solution of KOH in ethanol is added dropwise. After addition, stirring is kept on for 1 h at 4-6° C., then the reaction is warmed to room temperature and stirred for 4 h. The completion of the reaction is tested by TLC. The solvent is concentrated at 44° C. to obtain a solid, and the residue is dissolved with 10 ml of water, extracted with ethyl acetate (10 ml*2). The aqueous layer is separated and is acidified with 6N hydrochloric acid under ice bath condition to pH 2, extracted with ethyl acetate (20 ml*3). The three extracts are combined, washed with saturated brine (60 ml*2), and dried with anhydrous $NaSO_4$. Suction Filtrated, the filtrate is concentrated to give a light pink oily substance, 0.86 g, and the yield is 78%. $^1$H-NMR (400 MHz, $CDCl_3$, δ ppm): δ 4.23-4.25 (2H, $CH_3CH_2$—), 3.59-3.62 (2H, epoxy ring), 1.27-1.31 (3H, $CH_3CH_2$—).

Step 1.5 Synthesis of (2S,3S)-3-(benzyl(phenyl)carbamoyl)oxirane-2-carboxylic acid ethyl ester (2S,3S)-epoxybutanedioic acid monoethyl ester (9.19 g, 57.4 mmol), HATU (24 g, 63.1 mmol) and anhydrous dichloromethane (300 ml) are added into a 500 ml three-necked flask under nitrogen protection, stirring on ice bath. After adding DIPEA (10.4 ml, 63.1 mmol) and stirred for 15 minutes, N-benzylaniline (10.51 g, 57.4 mmol) is added. Stirred for 3 hours under ice bath, the reaction is complete. The reaction is diluted with 300 ml of ice water, standing layered, and the organic phase is separated. The organic layer is washed with water (300 ml*2), 0.5M HCl aqueous solution (150 ml*2), saturated $NaHCO_3$ (150 ml*2), and saturated brine (150 ml*2), and dried with anhydrous $NaSO_4$. Suction filtered, the filtrate is concentrated to give crude product 28.11 g. After column chromatography under reduced pressure, eluting with petroleum ether/ethyl acetate=6:1, 5:1, 4:1 to give pure white floc 15.13 g, and the yield is 81%.

Step 1.6 Synthesis of (2S,3S)-3-(benzyl(phenyl)carbamoyl)oxirane-2-carboxylic acid The (2S,3S)-3-(benzyl(phenyl)carbamoyl)oxirane-2-carboxylic acid ethyl ester (1.0 g, 3.1 mmol) and ethanol (25 ml) are added into 250 ml of eggplant-shaped flask and stirred, a mixed solution of KOH (0.21 g, 3.72 mmol) and ethanol (25 ml) is added under ice bath, followed by stirring at room temperature for 2.5 hours. The reaction is complete. The reaction solution is concentrated, dissolved with 20 ml of water. The aqueous phase is extracted with ethyl acetate (20 ml*2) and the aqueous layer is separated. The aqueous layer is acidified with 0.5M hydrochloric acid to pH 2 under ice bath and is the aqueous phase is extracted with ethyl acetate (30 ml*3). The organic phases are combined, washed with water (90 ml*2) and saturated brine (90 ml*2), and dried with anhydrous $NaSO_4$. Suction filtered, the filtrate is concentrated to give a white solid of 0.82 g, and the yield is 89%.

Step 1.7 Synthesis of (2S,3S)—$N^2$-benzyl-$N^2$-phenyl-$N^3$-(3,4-dimethoxyphenyl)-2,3-epoxybutanediamide (2S,3S)-3-(benzyl(phenyl)carbamoyl)oxirane-2-carboxylic acid (0.3 g, 1 mmol), HATU (0.42 g, 1.1 mmol) and anhydrous dichloromethane (10 ml) are added to a 50 ml nitrogen protected three-necked flask, and stirred on ice bath. After adding DIPEA (0.18 ml, 1.1 mmol) and stirred for 15 minutes, 3,4-dimethoxyaniline (0.15 g, 1 mmol) is added, stirred for 3 hours under ice bath. The reaction is complete. The reaction solution is diluted with 10 ml of ice water, standing layered, and the organic phase is separated. The organic phase is washed with water (10 ml*2), 0.5M HCl aqueous solution (10 ml*2), saturated $NaHCO_3$ (10 ml*2), saturated brine (10 ml*2), and dried with anhydrous $NaSO_4$. Suction filtered, the filtrate is concentrated to give a crude product. The crude product is recrystallized from ethanol to give 0.3 g of a white solid, and the yield is 70%. $[α]_D^{21.9}$=−57.545; $^1$H-NMR (400 MHz, DMSO-d6, δ ppm) δ 10.28 (s, 1H), 7.38-7.18 (m, 12H), 7.05-7.02 (dd, 1H, J=8.4 Hz, J=2.5 Hz), 6.89-6.87 (d, 1H, J=8.7 Hz), 3.79 (d, 1H, J=1.7 Hz), 3.70 (d, 6H, J=6.4 Hz), 3.31 (d, 1H, J=2.0 Hz); ESI-MS (m/z): $[M+H]^+$ 433.3. m.p. 156.5-157.2° C.

The following compounds can be prepared by referring to the method of step 1.7 of Example 1 with different reactants (various substituted aromatic amines) instead of 3,4-dimethoxyaniline in step 1.7.

Example 2

Synthesis of (2S,3S)—$N^2$-benzyl-$N^2$-phenyl-$N^3$-(2-thiazolyl)-2,3-epoxybutanediamide (Compound 2)

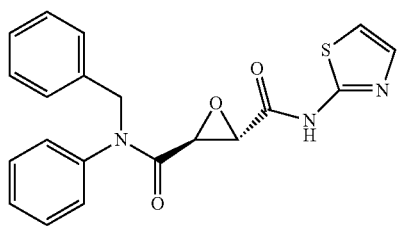 [SMILES: O=C(Nc1nccs1)[C@H]1O[C@@H]1C(=O)N(Cc1ccccc1)c1ccccc1]

Referring to the preparation method of step 1.7 of Example 1, the title compound is obtained by using 2-amino-thiazole instead of 3,4-dimethoxyaniline in step 1.7. The title compound is a white solid, and the yield is 50%. $[α]_D^{21.0}$=−23.909; $^1$H-NMR (400 MHz, $CDCl_3$-d, δ ppm) δ 7.53 (d, 1H, J=3.7 Hz), 7.35-7.26 (m, 6H), 7.19-7.17 (m, 2H), 7.06-7.05 (m, 2H, J=6.4 Hz), 7.00 (d, 1H, J=3.6 Hz), 4.95 (s, 2H), 4.07 (d, 1H, J=1.7 Hz), 3.38 (d, 1H, J=1.7 Hz); ESI-MS (m/z): $[M+H]^+$ 380.1. m.p. 146.6-147.4° C.

Example 3

Synthesis of (2S,3S)—N²-benzyl-N²-phenyl-N³-(3,4-dichlorophenyl)-2,3-epoxybutanediamide (Compound 3)

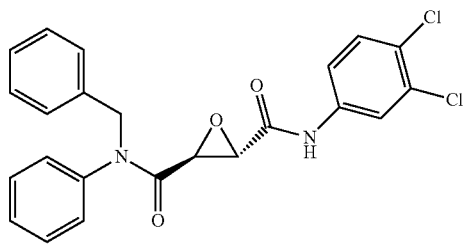 [SMILES: O=C(Nc1ccc(Cl)c(Cl)c1)[C@H]1O[C@@H]1C(=O)N(Cc1ccccc1)c1ccccc1]

Referring to the preparation method of step 1.7 of Example 1, the 3,4-dimethoxyaniline is replaced with 3,4-dichloroaniline to give a white solid of 0.23 g, and the yield is 52%. $[\alpha]_D^{22.4}$=−58.613 (c=1.0, methanol); ¹H-NMR (400 MHz, DMSO-d6, δ ppm) δ 10.69 (s, 1H), 7.89 (d, 1H, J=2.5 Hz), 7.60 (d, 1H, J=9.0 Hz), 7.48-7.45 (dd, 1H, J=9.0 Hz, J=2.5 Hz), 7.38-7.19 (m, 10H), 5.08 (d, 1H, J=5.1 Hz), 4.86 (d, 1H, J=4.8 Hz), 3.84 (d, 1H, J=2.0 Hz), 3.34 (d, 1H, J=1.7 Hz); ESI-MS (m/z): [M+H]⁺ 441.0. m.p. 174.5-175.7° C.

Example 4

Synthesis of (2S,3S)—N²-benzyl-N²-phenyl-N³-(3-fluorophenyl)-2,3-epoxybutanediamide (Compound 4)

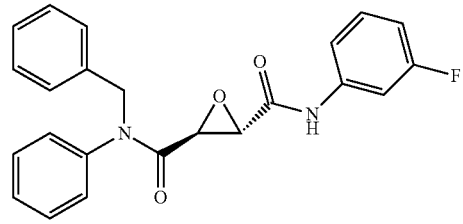 [SMILES: O=C(Nc1cccc(F)c1)[C@H]1O[C@@H]1C(=O)N(Cc1ccccc1)c1ccccc1]

Referring to the preparation method of step 1.7 of Example 1, the 3,4-dimethoxyaniline is replaced with 3-fluoroaniline to give a white solid of 0.22 g, and the yield is 56%. $[\alpha]_D^{22.4}$=−67.636 (c=1.0, methanol); ¹H-NMR (400 MHz, CDCl₃-d, δ ppm) δ 7.67 (s, 1H), 7.43-7.33 (m, 4H), 7.29-7.26 (m, 6H), 7.10-7.08 (m, 2H), 7.05-7.03 (dd, 1H, J=8.1 Hz, J=1.1 Hz), 6.83-6.78 (m, 1H), 5.03 (d, 1H, J=14.0 Hz), 4.91 (d, 1H, J=14.0 Hz), 3.89 (d, 1H, J=2.2 Hz), 3.31 (d, 1H, J=2.2 Hz); ESI-MS (m/z): [M+H]⁺ 391.4. m.p. 180.5-182.0° C.

Example 5

Synthesis of (2S,3S)—N²-benzyl-N²-phenyl-N³-(4-fluorophenyl)-2,3-epoxybutanediamide (Compound 5)

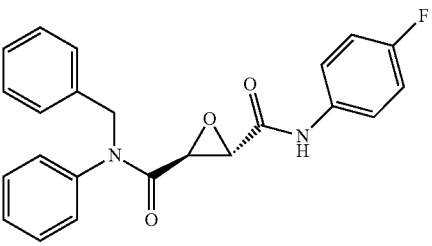 [SMILES: O=C(Nc1ccc(F)cc1)[C@H]1O[C@@H]1C(=O)N(Cc1ccccc1)c1ccccc1]

Referring to the preparation method of step 1.7 of Example 1, the 3,4-dimethoxyaniline is replaced with 4-fluoroaniline to give a white solid of 0.13 g, and the yield is 33%. $[\alpha]_D^{21.3}$=−64.589 (c=1.0, methanol); ¹H-NMR (400 MHz, CDCl₃-d, δ ppm) δ 7.60 (s, 1H), 7.38-6.98 (m, 14H), 5.03 (d, 1H, J=14.3 Hz), 4.92 (d, 1H, J=14.2 Hz), 3.90 (s, 1H), 3.32 (s, 1H); ESI-MS (m/z): [M+H]⁺ 391.4. m.p. 153.8-154.7° C.

Example 6

Synthesis of (2S,3S)—N²-benzyl-N²-phenyl-N³-(2-fluorophenyl)-2,3-epoxybutanediamide (Compound 6)

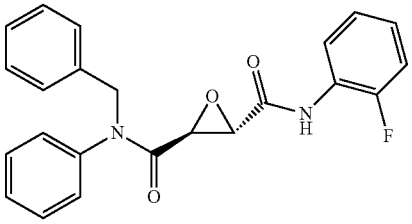 [SMILES: O=C(Nc1ccccc1F)[C@H]1O[C@@H]1C(=O)N(Cc1ccccc1)c1ccccc1]

Referring to the preparation method of step 1.7 of Example 1, the 3,4-dimethoxyaniline is replaced with 2-fluoroaniline to give a white solid of 0.19 g, and the yield is 49%. $[\alpha]_D^{22.3}$=−76.626 (c=1.0, methanol); ¹H-NMR (400 MHz, CDCl₃-d, δ ppm) δ 8.17 (t, 1H), 7.85 (s, 1H), 7.37-7.33 (m, 3H), 7.29-7.26 (m, 4H), 7.20-7.18 (m, 2H), 7.11-7.02 (m, 5H), 5.02 (d, 1H, J=14.3 Hz), 4.93 (d, 1H, J=14.2 Hz), 3.91 (d, 1H, J=1.7 Hz), 3.33 (d, 1H, J=2.0 Hz); ESI-MS (m/z): [M+H]⁺ 391.3. m.p. 139.2-140.3° C.

Example 7

Synthesis of (2S,3S)—N²-benzyl-N²-phenyl-N³-(3-methoxyphenyl)-2,3-epoxybutanediamide (Compound 7)

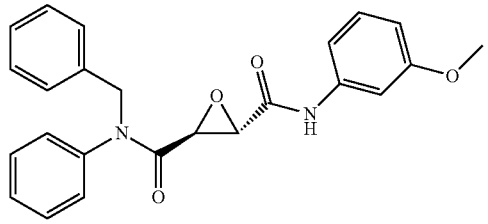 [SMILES: COc1cccc(NC(=O)[C@H]2O[C@@H]2C(=O)N(Cc2ccccc2)c2ccccc2)c1]

Referring to the preparation method of step 1.7 of Example 1, the 3,4-dimethoxyaniline is replaced with 3-methoxyaniline to give a white solid of 0.26 g, and the yield is 65%. $[\alpha]_D^{21.5}=-60.627$; $^1$H-NMR (400 MHz, CDCl$_3$-d, δ ppm) δ 7.59 (s, 1H), 7.39-7.32 (m, 3H), 7.29-7.26 (m, 3H), 7.19-7.15 (m, 4H), 7.10 (d, 1H, J=7.8 Hz), 6.90 (d, 1H, J=8.1 Hz), 5.03 (d, 1H, J=14.3 Hz), 4.91 (d, 1H, J=14.3 Hz), 3.89 (d, 1H, J=1.4 Hz), 3.77 (s, 3H), 3.31 (s, 1H); ESI-MS (m/z): [M+H]$^+$ 403.4. m.p. 130.7-131.7° C.

Example 8

Synthesis of (2S,3S)—N²-benzyl-N²-phenyl-N³-(3-chlorophenyl)-2,3-epoxybutanediamide (Compound 8)

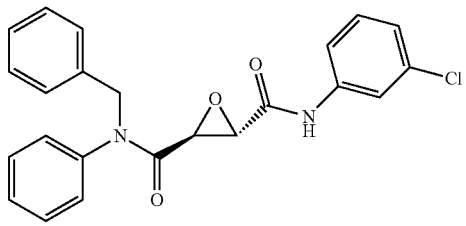 [SMILES: O=C(Nc1cccc(Cl)c1)[C@H]1O[C@@H]1C(=O)N(Cc1ccccc1)c1ccccc1]

Referring to the preparation method of step 1.7 of Example 1, the 3,4-dimethoxyaniline is replaced with 3-chloroaniline to give a white solid of 0.28 g, and the yield is 68%. $[\alpha]_D^{22.4}=-60.399$ (c=1.0, methanol); $^1$H-NMR (400 MHz, CDCl$_3$-d, δ ppm) 7.66 (s, 1H), 7.56 (d, 1H, J=1.7 Hz), 7.38-7.06 (m, 13H), 5.02 (d, 1H, J=14.3 Hz), 4.92 (d, 1H, J=14.0 Hz), 3.90 (d, 1H, J=2.0 Hz), 3.32 (d, 1H, J=2.0 Hz); ESI-MS (m/z): [M+H]$^+$ 407.5. m.p. 179.2-179.6° C.

Example 9

Synthesis of (2S,3S)—N²-benzyl-N²-phenyl-N³-(4-nitrophenyl)-2,3-epoxybutanediamide (Compound 9)

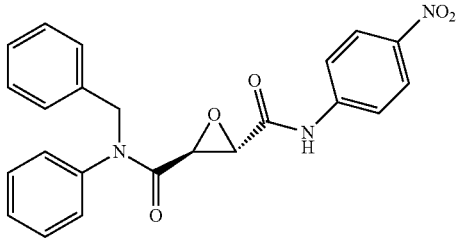 [SMILES: O=C(Nc1ccc([N+](=O)[O-])cc1)[C@H]1O[C@@H]1C(=O)N(Cc1ccccc1)c1ccccc1]

Referring to the preparation method of step 1.7 of Example 1, the 3,4-dimethoxyaniline is replaced with 4-nitroaniline to give a white solid of 0.28 g, and the yield is 60%. $[\alpha]_D^{22.2}=-63.315$ (c=1.0, methanol); $^1$H-NMR (400 MHz, CDCl$_3$-d, δ ppm) δ 8.17 (m, 2H), 8.02 (s, 1H), 7.65-7.62 (m, 2H), 7.40-7.34 (m, 3H), 7.30-7.26 (m, 3H), 7.19-7.17 (m, 2H), 7.11-7.09 (m, 2H), 5.02 (d, 1H, J=14.3 Hz), 4.93 (d, 1H, J=14.3 Hz), 3.95 (d, 1H, J=1.9 Hz), 3.37 (d, 1H, J=1.9 Hz); ESI-MS (m/z): [M+H]$^+$ 418.5. m.p. 160.2-161.3° C.

Example 10

Synthesis of (2S,3S)—N²-benzyl-N²-phenyl-N³-(2,3-dichlorophenyl)-2,3-epoxybutanediamide (Compound 10)

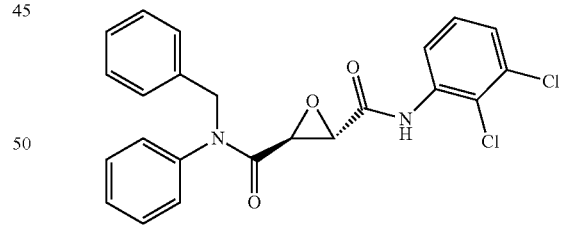

Referring to the preparation method of step 1.7 of Example 1, the 3,4-dimethoxyaniline is replaced with 2,3-dichloroaniline to give a white solid of 0.23 g, and the yield is 52%. $[\alpha]_D^{21.4}=-66.207$ (c=1.0, methanol); $^1$H-NMR (400 MHz, CDCl$_3$-d, δ ppm) δ 8.25 (s, 1H), 8.16 (m, 1H), 7.39-7.26 (m, 6H), 7.21-7.08 (m, 6H), 5.01 (d, 1H, J=14.3 Hz), 4.94 (d, 1H, J=14.3 Hz), 3.94 (d, 1H, J=2.0 Hz), 3.34 (d, 1H, J=2.0 Hz); ESI-MS (m/z): [M+H]$^+$ 441.5. m.p. 115.7-115.8° C.

Example 11

Synthesis of (2S,3S)—N²-benzyl-N²-phenyl-N³-(2-chlorophenyl)-2,3-epoxybutanediamide (Compound 11)

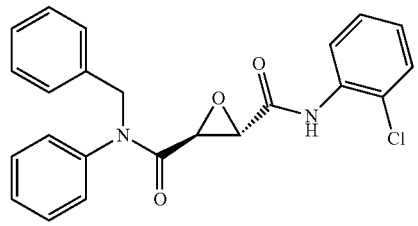 [SMILES: O=C(Nc1ccccc1Cl)[C@H]1O[C@@H]1C(=O)N(Cc1ccccc1)c1ccccc1]

Referring to the preparation method of step 1.7 of Example 1, the 3,4-dimethoxyaniline is replaced with 2-chloroaniline to give a white solid of 0.21 g, and the yield is 51%. $[\alpha]_D^{22.9}=-70.947$ (c=1.0, methanol); ¹H-NMR (400 MHz, DMSO-d6, δ ppm) δ 10.00 (s, 1H), 7.51 (m, 2H), 7.38-7.21 (m, 12H), 5.09 (d, 1H, J=14.8 Hz), 4.86 (d, 1H, J=14.8 Hz), 3.99 (d, 1H, J=2.0 Hz), 3.34 (d, 1H, J=2.0 Hz); ESI-MS (m/z): [M+H]⁺ 407.5. m.p. 117.3-118.2° C.

Example 12

Synthesis of (2S,3S)—N²-benzyl-N²-phenyl-N³-(4-chlorophenyl)-2,3-epoxybutanediamide (Compound 12)

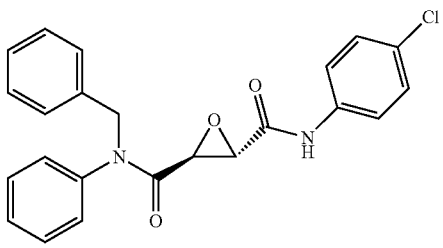 [SMILES: O=C(Nc1ccc(Cl)cc1)[C@H]1O[C@@H]1C(=O)N(Cc1ccccc1)c1ccccc1]

Referring to the preparation method of step 1.7 of Example 1, the 3,4-dimethoxyaniline is replaced with 4-chloroaniline to give a white solid of 0.12 g, and the yield is 29%. $[\alpha]_D^{21.9}=-67.936$ (c=1.0, methanol); ¹H-NMR (400 MHz, DMSO-d6, δ ppm) δ 10.55 (s, 1H), 7.54-7.28 (m, 14H), 5.09 (d, 1H, J=15.1 Hz), 4.85 (d, 1H, J=14.8 Hz), 3.83 (d, 1H, J=2.0 Hz), 3.32 (d, 1H, J=2.0 Hz); ESI-MS (m/z): [M+H]⁺ 407.3. m.p. 175.2-175.8° C.

Example 13

Synthesis of (2S,3S)—N²-benzyl-N²-phenyl-N³-(2-methyl-3-chlorophenyl)-2,3-epoxybutanediamide (Compound 13)

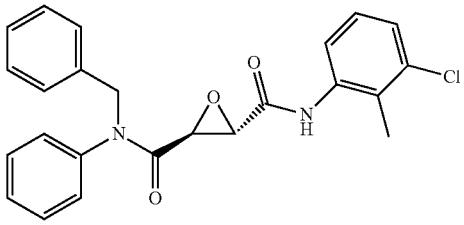 [SMILES: Cc1c(Cl)cccc1NC(=O)[C@H]1O[C@@H]1C(=O)N(Cc1ccccc1)c1ccccc1]

Referring to the preparation method of step 1.7 of Example 1, the 3,4-dimethoxyaniline is replaced with 2-methyl-3-chloroaniline to give a white solid of 0.36 g, and the yield is 86%. $[\alpha]_D^{22.9}=-63.711$ (c=1.0, methanol); ¹H-NMR (400 MHz, DMSO-d6, δ ppm) δ 10.02 (s, 1H), 7.40-7.17 (m, 13H), 5.09 (d, 1H, J=14.8 Hz), 4.86 (d, 1H, J=14.8 Hz), 3.89 (d, 1H, J=2.0 Hz), 3.38 (d, 1H, J=2.0 Hz); ESI-MS (m/z): [M+H]⁺ 421.5. m.p. 119.4-120.2° C.

Example 14

Synthesis of (2S,3S)—N²-benzyl-N²-phenyl-N³-(3-bromophenyl)-2,3-epoxybutanediamide (Compound 14)

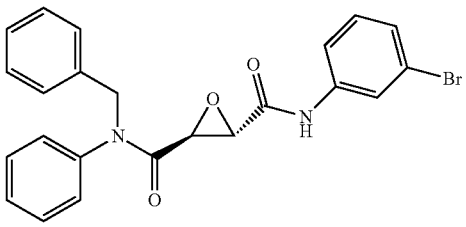 [SMILES: O=C(Nc1cccc(Br)c1)[C@H]1O[C@@H]1C(=O)N(Cc1ccccc1)c1ccccc1]

Referring to the preparation method of step 1.7 of Example 1, the 3,4-dimethoxyaniline is replaced with 3-bromoaniline to give a white solid of 0.41 g, and the yield is 91%. $[\alpha]_D^{22.9}=-50.917$ (c=1.0, methanol); ¹H-NMR (400 MHz, CDCl₃-d, δ ppm) δ 7.69 (m, 2H), 7.40-7.08 (m, 12H), 5.02 (d, 1H, J=14.3 Hz), 4.92 (d, 1H, J=14.3 Hz), 3.90 (d, 1H, J=1.9 Hz), 3.32 (d, 1H, J=1.9 Hz); ESI-MS (m/z): [M+H]⁺ 451.5. m.p. 177.5-178.2° C.

Example 15

Synthesis of (2S,3S)—N²-benzyl-N²-phenyl-N³-(2-bromophenyl)-2,3-epoxybutanediamide (Compound 15)

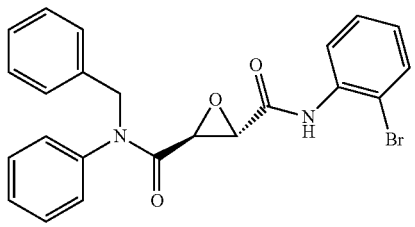

Referring to the preparation method of step 1.7 of Example 1, the 3,4-dimethoxyaniline is replaced with 2-bromoaniline to give a white solid of 0.36 g, and the yield is 80%. $[\alpha]_D^{22.9}=-53.027$ (c=1.0, methanol); ¹H-NMR (400 MHz, CDCl₃-d, δ ppm) δ 8.17 (d, 2H, J=8.1 Hz), 7.49 (d, 1H, J=1.4 Hz), 7.48-7.26 (m, 7H), 7.20-6.96 (m, 5H), 5.02-4.92 (dd, 2H, J=14.3 Hz, J=2.7 Hz), 3.93 (d, 1H, J=2.0 Hz), 3.37 (d, 1H, J=2.0 Hz); ESI-MS (m/z): [M+H]⁺ 451.5. m.p. 113.2-114.3° C.

Example 16

Synthesis of (2S,3S)-3-((4-(benzo[d]thiazol-2-ylcarbamoyl)phenyl)(4-fluorobenzyl)carbamoyl)oxirane-2-carboxylic acid (Compound 16)

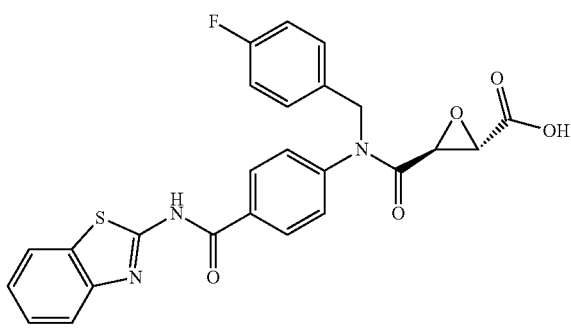 [SMILES: O=C(Nc1nc2ccccc2s1)c1ccc(N(Cc2ccc(F)cc2)C(=O)[C@H]2O[C@@H]2C(=O)O)cc1]

Step 16.1 Synthesis of the Intermediate N-(benzo[d]thiazol-2-yl)-4-nitrobenzamide 100 ml three-neck flask is charged with a p-nitrobenzoyl chloride (5.57 g, 30 mmol) and anhydrous dichloromethane (15 ml), and the opening of the flask is equipped with a thermometer, drying tube and a constant pressure dropping funnel. The mixed solution of 2-aminobenzothiazole (3.00 g, 20 mmol), triethylamine (4.17 ml, 30 mmol) and anhydrous dichloromethane (15 ml) is added dropwise under ice bath, and the temperature is controlled at 0-5° C. for 1 hour, followed by reaction at room temperature overnight. A large quantity of yellow solid is precipitated and suction filtered, and the filter cake is washed twice with water, dried to give the yellow solid crude product of 5.3 g, and the yield is 88.5%. The crude product is used directly in the next step.

Step 16.2 Synthesis of the Intermediate N-(benzo[d]thiazol-2-yl)-4-amino-benzamide The N-(benzo[d]thiazol-2-yl)-4-nitrobenzamide (1 g, 3.34 mmol), stannous chloride dihydrate (3 g, 13.36 mmol) and methanol/glacial acetic acid (29 ml/10 ml) are added in a 250 ml eggplant-shaped flask, heated and refluxed at 70° C. for 2 hours. The reaction is complete. The reaction mixture is concentrated, and water is added (80 ml) to dilute, and saturated potassium carbonate solution is added dropwise with stirring, adjusting pH to 8-9, generating a large amount of bubbles. The aqueous solution is extracted with ethyl acetate (80 ml*3), and the organic phases are combined, washed with water (240 ml*2) and saturated brine (240 ml*2), and dried with anhydrous NaSO₄. Suction filtered, the filtrate is concentrated to give the crude product as a yellow solid. The crude product is recrystallized (ethanol (20 ml/g)), to give a yellow solid of 0.66 g, and the yield is 73%.

Step 16.3 Synthesis of the Intermediate N-(benzo[d]thiazol-2-yl)-4-(4-fluorobenzyl)benzamide The N-(benzo[d]thiazol-2-yl)-4-aminobenzamide (1 g, 3.7 mmol), p-fluorobenzaldehyde (0.44 ml, 4.1 mmol) and 30 ml of methanol are placed into a 100 ml eggplant-shaped flask, and tetraisopropyl titanate (1.3 ml, 4.4 mmol) is added on ice bath with stirring, stirred at room temperature overnight. Sodium cyanoborohydride (0.58 g, 9.25 mmol) is added the next day, stirred at room temperature for 10 hours. The mixed solution of ethyl acetate/water (3:1, 40 ml) is added to quench and dilute the reaction solution. Suction filtered through Celite, the filter cake is washed several times with ethyl acetate, and the filtrate is washed twice with saturated brine, and dried with anhydrous NaSO₄. Suction filtered, the filtrate is concentrated to give the crude product as a yellow solid. After column chromatography under reduced pressure, eluting with methylene chloride to give a white solid of 1.1 g, and the yield is 78%.

Step 16.4 Synthesis of the Intermediate (2S,3S)-3-((4-(benzo[d]thiazol-2-ylcarbamoyl)phenyl)(4-fluorobenzyl)carbamoyl)oxirane-2-carboxylic ethyl ester (2S,3S)-epoxybutanedioic acid monoethyl ester (0.93 g, 5.8 mmol), anhydrous tetrahydrofuran (50 ml) and triethylamine (1 ml, 6.4 mmol) are added in a 250 ml three-necked flask under nitrogen protection. Under ice bath with stirring, oxalyl chloride (0.61 ml, 6.4 mmol) dissolved in 60 ml of tetrahydrofuran is added dropwise. The reaction mixture is changed from clear to white suspension. When dropping is completed, the mixture is stirred at room temperature for 3.5 hours, and then the solvent is concentrated to give a white solid powder. Dissolved with 30 ml of dichloromethane under nitrogen atmosphere, the solution is added in three-necked flask charged with N-(benzo[d]thiazol-2-yl)-4-(4-fluorobenzylamino)benzamide (0.87 g, 2.3 mmol), triethylamine (1 ml, 6.4 mmol) and anhydrous dichloromethane (20 ml). When dropping is completed, the mixture is stirred at room temperature for 1.5 hours. During this period, the white suspension gradually turns yellow transparent solution and finally to red transparent solution. After completion of the reaction, the mixture is diluted with ice water, extracted with ethyl acetate, and the organic phase is washed twice with 0.5M aqueous HCl, twice with saturated NaHCO₃, and twice with saturated brine, and dried with anhydrous NaSO₄. Suction filtered, the filtrate is concentrated to give the crude product as a brown solid powder of 1.31 g. The crude product is used directly in the next step.

Step 16.5 Synthesis of (2S,3S)-3-((4-(benzo[d]thiazol-2-ylcarbamoyl)phenyl)(4-fluorobenzyl)carbamoyl)oxirane-2-carboxylic acid (2S,3S)-3-((4-(benzo[d]thiazol-2-ylcarbamoyl)phenyl) (4-fluorobenzyl)carbamoyl)oxirane-2-carboxylic ethyl ester (1.31 g, 2.5 mmol) and ethanol (15 ml) are placed into a 100 ml eggplant-shaped flask with stirring, and a mixed solution of KOH (0.28 g, 5 mmol) and ethanol (15 ml) is added under ice bath. The reaction is stirred at room temperature, and then the reaction is complete. The reaction solution is concentrated to give a tan solid, which is dissolved in 40 ml of water. The aqueous phase is extracted with ethyl acetate (30 ml*2), and the aqueous layer is separated and acidified by 0.5 M hydrochloric acid to pH 2 under ice bath, and a large amount of solid is precipitated. The solid is suction filtered, washed twice with water and twice with ethyl acetate to give a pale pink solid of 0.98 g, and the yield is 80%. $^1$H-NMR (400 MHz, DMSO-d6, δ ppm) δ 13.38 (s, 1H), 12.91 (s, 1H), 8.18 (d, 2H, J=8.4 Hz), 8.03 (d, 1H, J=7.9 Hz), 7.80 (d, 1H, J=7.8 Hz), 7.54-7.49 (m, 3H), 7.37-7.28 (m, 3H), 7.16-7.12 (m, 2H), 5.09-4.95 (m, 2H), 3.72 (d, 1H, J=1.4 Hz), 3.41 (s, 1H); ESI-MS (m/z): [M−H]$^-$ 490.5 m.p. 200.6-201.3° C.

Example 17

Synthesis of (2S,3S)—N$^2$-(4-(benzo[d]thiazol-2-ylcarbamoyl)phenyl)-N$^3$-(3,4-dimethoxyphenyl)-N$^2$-(4-fluorobenzyl)-2,3-epoxybutanediamide (Compound 17)

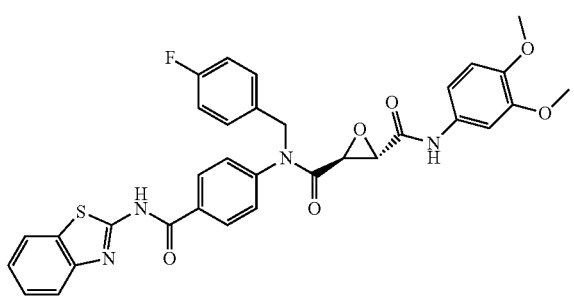 [SMILES: COc1ccc(NC(=O)[C@H]2O[C@@H]2C(=O)N(Cc2ccc(F)cc2)c2ccc(C(=O)Nc3nc4ccccc4s3)cc2)cc1OC]

Referring to the preparation method of step 1.7 of Example 1, the (2S,3S)-3-(benzyl(phenyl)carbamoyl)oxirane-2-carboxylic acid is replaced with (2S,3S)-3-((4-(benzo[d]thiazol-2-yl)carbamoyl)phenyl(4-fluorobenzyl) carbamoyl-2-carboxylic acid to give a white solid of 0.18 g, and the yield is 35%. $^1$H-NMR (400 MHz, DMSO-d6, δ ppm) δ 12.90 (s, 1H), 10.29 (s, 1H), 8.16 (d, 2H, J=8.7 Hz), 8.03-6.85 (m, 13H), 5.13 (d, 1H, J=15.1 Hz), 4.96 (d, 1H, J=15.7 Hz), 3.83 (s, 1H), 3.67 (d, 6H, J=14.6 Hz), 3.45 (s, 1H); ESI-MS (m/z): [M+H]$^+$ 627.5. m.p. 205.6-206.3° C.

Example 18

Synthesis of (2S,3S)—N$^2$-(4-(benzo[d]thiazol-2-ylcarbamoyl)phenyl)-N$^3$-(3-bromophenyl)-N$^2$-(4-fluorobenzyl)-2,3-epoxybutanediamide (Compound 18)

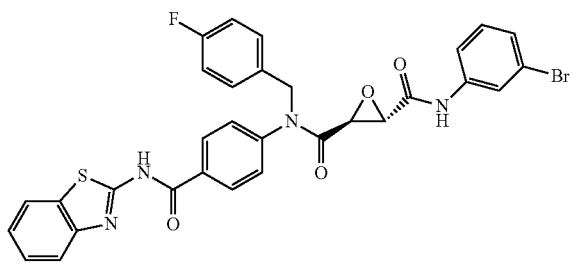

Referring to the preparation method of step 1.7 of Example 1, the 3,4-dimethoxyaniline is replaced with 3-bromoaniline and the (2S,3S)-3-(benzyl(phenyl)carbamoyl) oxirane-2-carboxylic acid is replaced with (2S,3S)-3-((4-(benzo[d]thiazol-2-ylcarbamoyl)phenyl)(4-fluorobenzyl) carbamoyl)oxirane-2-carboxylic acid to give a white solid of 0.16 g, and the yield is 31%. $^1$H-NMR (400 MHz, DMSO-d6, δ ppm) δ 12.90 (s, 1H), 10.59 (s, 1H), 8.16-7.13 (m, 16H), 5.14 (d, 1H, J=15.1 Hz), 4.96 (d, 1H, J=14.0 Hz), 3.88 (s, 1H), 3.48 (s, 1H); ESI-MS (m/z): [M+H]$^+$ 645.2. m.p. 206.3-207.1° C.

Example 19

Synthesis of (2S,3S)—N$^2$-(4-(benzo[d]thiazol-2-ylcarbamoyl)phenyl)-N$^3$-(4-chlorophenyl)-N$^2$-(4-fluorobenzyl)-2,3-epoxybutanediamide (Compound 19)

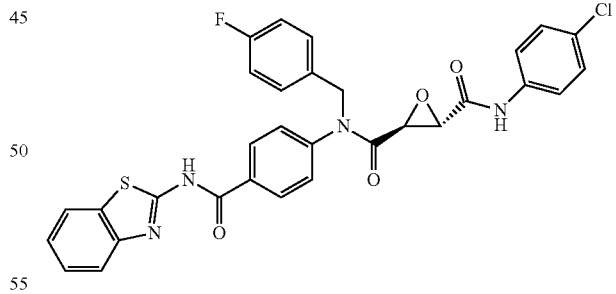

Referring to the preparation method of step 1.7 of Example 1, the 3,4-dimethoxyaniline is replaced with 4-chloroaniline and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.21 g, and the yield is 43%. $^1$H-NMR (400 MHz, DMSO-d6, δ ppm) δ 12.89 (s, 1H), 10.55 (s, 1H), 8.15-7.13 (m, 16H), 5.13 (d, 1H, J=15.4 Hz), 4.95 (d, 1H, J=15.4 Hz), 3.87 (s, 1H), 3.47 (s, 1H); ESI-MS (m/z): [M+H]$^+$ 601.5. m.p. 198.7-199.5° C.

Example 20

Synthesis of (2S,3S)—N²-(4-(benzo[d]thiazol-2-ylcarbamoyl)phenyl)-N³-(4-methoxyphenyl)-N²-(4-fluorobenzyl)-2,3-epoxybutanediamide (Compound 20)

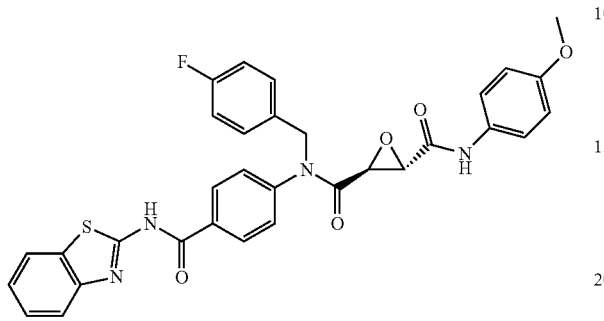

Referring to the preparation method of step 1.7 of Example 1, the 3,4-dimethoxyaniline is replaced with 4-methoxyaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.17 g, and the yield is 35%. ¹H-NMR (400 MHz, DMSO-d6, δ ppm) δ 12.91 (s, 1H), 10.29 (s, 1H), 8.16-6.83 (m, 16H), 5.13 (d, 1H, J=15.4 Hz), 4.96 (d, 1H, J=15.4 Hz), 3.83 (s, 1H), 3.45 (s, 1H); ESI-MS (m/z): [M−H]⁻ 595.7. m.p. 200.1-201.2° C.

Example 21

Synthesis of (2S,3S)—N²-(4-(benzo[d]thiazol-2-ylcarbamoyl)phenyl)-N³-(3-methoxyphenyl)-N²-(4-fluorobenzyl)-2,3-epoxybutanediamide (Compound 21)

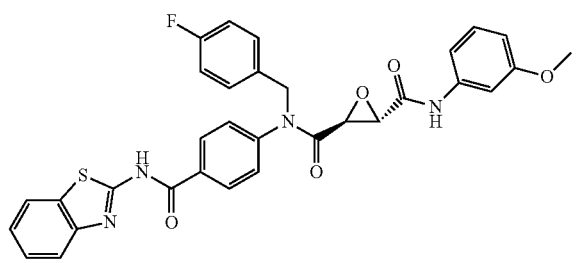 [SMILES: COc1cccc(NC(=O)[C@H]2O[C@@H]2C(=O)N(Cc2ccc(F)cc2)c2ccc(C(=O)Nc3nc4ccccc4s3)cc2)c1]

Referring to the preparation method of step 1.7 of Example 1, the 3,4-dimethoxyaniline is replaced with 3-methoxyaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.17 g, and the yield is 35%. ¹H-NMR (400 MHz, DMSO-d6, δ ppm) δ 12.90 (s, 1H), 10.43 (s, 1H), 8.16-6.61 (m, 16H), 5.14 (d, 1H, J=14.8 Hz), 4.96 (d, 1H, J=15.4 Hz), 3.88 (s, 1H), 3.67 (s, 3H), 3.46 (s, 1H); ESI-MS (m/z): [M−H]⁻ 595.7. m.p. 223.1-224.1° C.

Example 22

Synthesis of (2S,3S)—N²-(4-(benzo[d]thiazol-2-ylcarbamoyl)phenyl)-N³-(3,4-difluorophenyl)-N²-(4-fluorobenzyl)-2,3-epoxybutanediamide (Compound 22)

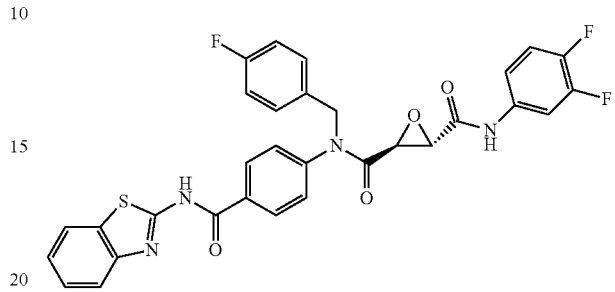

Referring to the preparation method of step 1.7 of Example 1, the 3,4-dimethoxyaniline is replaced with 3,4-dichloroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.07 g, and the yield is 14%. ¹H-NMR (400 MHz, DMSO-d6, δ ppm) δ 12.90 (s, 1H), 10.43 (s, 1H), 8.16-6.61 (m, 16H), 5.14 (d, 1H, J=14.8 Hz), 4.96 (d, 1H, J=15.4 Hz), 3.88 (s, 1H), 3.67 (s, 3H), 3.46 (s, 1H); ESI-MS (m/z): [M+H]⁺ 603.4. m.p. 219.2-219.7° C.

Example 23

Synthesis of (2S,3S)—N²-(4-(benzo[d]thiazol-2-ylcarbamoyl)phenyl)-N³-(3-chlorophenyl)-N²-(4-fluorobenzyl)-2,3-epoxybutanediamide (Compound 23)

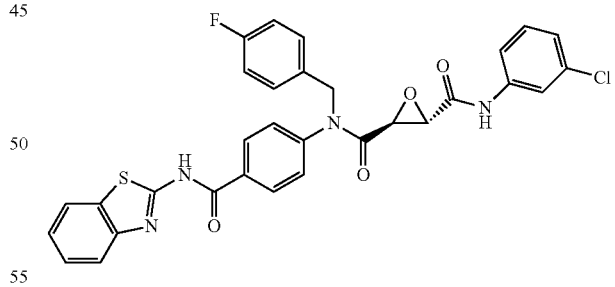

Referring to the preparation method of step 1.7 of Example 1, the 3,4-dimethoxyaniline is replaced with 3-chloroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.16 g, and the yield is 33%. ¹H-NMR (400 MHz, DMSO-d6, δ ppm) δ 12.90 (s, 1H), 10.60 (s, 1H), 8.16-7.11 (m, 16H), 5.13 (d, 1H, J=15.1 Hz), 4.96 (d, 1H, J=14.9 Hz), 3.88 (s, 1H), 3.48 (s, 1H); ESI-MS (m/z): [M−H]⁻ 599.5. m.p. 209.8-210.3° C.

Example 24

Synthesis of (2S,3S)—N²-(4-(benzo[d]thiazol-2-ylcarbamoyl)phenyl)-N³-(4-nitrophenyl)-N²-(4-fluorobenzyl)-2,3-epoxybutanediamide (Compound 24)

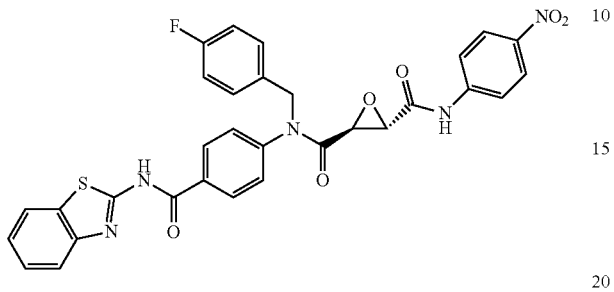

Referring to the preparation method of step 1.7 of Example 1, the 3,4-dimethoxyaniline is replaced with 4-nitroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.03 g, and the yield is 6%. $[\alpha]_D^{22.7}$=−61.212 (c=1.0, methanol); ¹H-NMR (400 MHz, DMSO-d6, δ ppm) δ 12.88 (s, 1H), 11.00 (s, 1H), 8.24-7.18 (m, 16H), 5.18 (d, 1H, J=14.8 Hz), 5.01 (d, 1H, J=14.0 Hz), 3.98 (s, 1H), 3.57 (s, 1H); ESI-MS (m/z): [M−H]⁻ 610.6. m.p. 203.5-204.2° C.

Example 25

Synthesis of (2S,3S)—N²-(4-(benzo[d]thiazol-2-ylcarbamoyl)phenyl)-N³-(2,3-dichlorophenyl)-N²-(4-fluorobenzyl)-2,3-epoxybutanediamide (Compound 25)

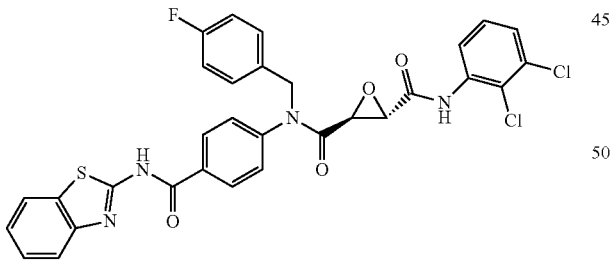

Referring to the preparation method of step 1.7 of Example 1, the 3,4-dimethoxyaniline is replaced with 2,3-dichloroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.04 g, and the yield is 8%. $[\alpha]_D^{22.5}$=−56.570 (c=1.0, methanol); ¹H-NMR (400 MHz, DMSO-d6, δ ppm) δ 12.95 (s, 1H), 10.19 (s, 1H), 8.24-7.18 (m, 15H), 5.16 (d, 1H, J=12.0 Hz), 4.97 (d, 1H, J=12.0 Hz), 4.07 (s, 1H), 3.51 (s, 1H); ESI-MS (m/z): [M+H]⁺ 635.6. m.p. 210.2-211.1° C.

Example 26

Synthesis of (2S,3S)—N²-(4-(benzo[d]thiazol-2-ylcarbamoyl)phenyl)-N³-(2,4-dichlorophenyl)-N²-(4-fluorobenzyl)-2,3-epoxybutanediamide (Compound 26)

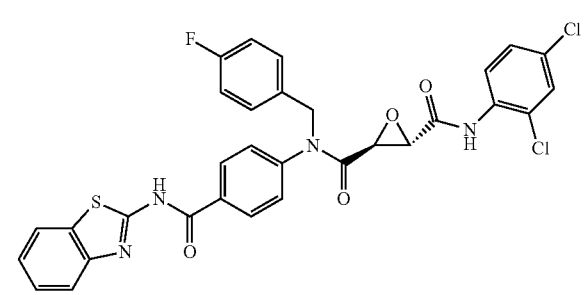 [SMILES: O=C(Nc1nc2ccccc2s1)c1ccc(N(Cc2ccc(F)cc2)C(=O)[C@H]2O[C@@H]2C(=O)Nc2ccc(Cl)cc2Cl)cc1]

Referring to the preparation method of step 1.7 of Example 1, the 3,4-dimethoxyaniline is replaced with 2,3-dichloroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.09 g, and the yield is 18%. $[\alpha]_D^{22.8}$=−73.974 (c=1.0, methanol); ¹H-NMR (400 MHz, DMSO-d6, δ ppm) δ 12.88 (s, 1H), 10.84 (s, 1H), 8.15-7.14 (m, 15H), 5.12 (d, 1H, J=15.1 Hz), 4.97 (d, 1H, J=15.4 Hz), 3.93 (s, 1H), 3.51 (s, 1H); ESI-MS (m/z): [M+H]⁺ 636.4. m.p. 206.7-207.5° C.

Example 27

Synthesis of (2S,3S)—N²-(4-(benzo[d]thiazol-2-ylcarbamoyl)phenyl)-N³-(2-bromophenyl)-N²-(4-fluorobenzyl)-2,3-epoxybutanediamide (Compound 27)

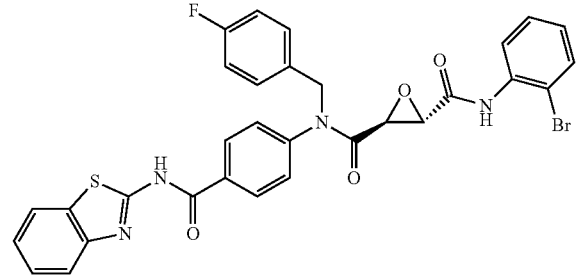 [SMILES: O=C(Nc1nc2ccccc2s1)c1ccc(N(Cc2ccc(F)cc2)C(=O)[C@H]2O[C@@H]2C(=O)Nc2ccccc2Br)cc1]

Referring to the preparation method of step 1.7 of Example 1, the 3,4-dimethoxyaniline is replaced with 2-bromoaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.05 g, and the yield is 10%. $[\alpha]_D^{21.8}$=−54.263 (c=1.0, methanol); ¹H-NMR (400 MHz, DMSO-d6, δ ppm) δ 12.94 (s, 1H), 9.93 (s, 1H), 8.19-7.12 (m, 15H), 5.14 (d, 1H, J=16.0 Hz), 4.96 (d, 1H, J=16.0 Hz), 3.98 (s, 1H), 3.34 (s, 1H); ESI-MS (m/z): [M+H]⁺ 645.5. m.p. 179.2-180.1° C.

Example 28

Synthesis of (2S,3S)—N²-(4-(benzo[d]thiazol-2-ylcarbamoyl)phenyl)-N³-(2-methyl-3-chlorophenyl)-N²-(4-fluorobenzyl)-2,3-epoxybutanediamide (Compound 28)

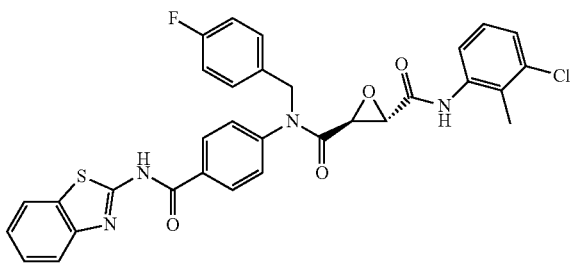 [SMILES: Cc1c(Cl)cccc1NC(=O)[C@H]1O[C@@H]1C(=O)N(Cc1ccc(F)cc1)c1ccc(C(=O)Nc2nc3ccccc3s2)cc1]

Referring to the preparation method of step 1.7 of Example 1, the 3,4-dimethoxyaniline is replaced with 2-methyl-3-chloroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.13 g, and the yield is 26%. ¹H-NMR (400 MHz, DMSO-d6, δ ppm) δ 12.95 (s, 1H), 10.03 (s, 1H), 8.19-7.12 (m, 15H), 5.14 (d, 1H, J=15.1 Hz), 4.96 (d, 1H, J=15.5 Hz), 3.93 (s, 1H), 3.47 (s, 1H), 2.07 (s, 3H); ESI-MS (m/z): [M−H]⁻ 613.4. m.p. 210.3-211.1° C.

Example 29

Synthesis of (2S,3S)—N²-(4-(benzo[d]thiazol-2-ylcarbamoyl)phenyl)-N³-(4-fluorophenyl)-N²-(4-fluorobenzyl)-2,3-epoxybutanediamide (Compound 29)

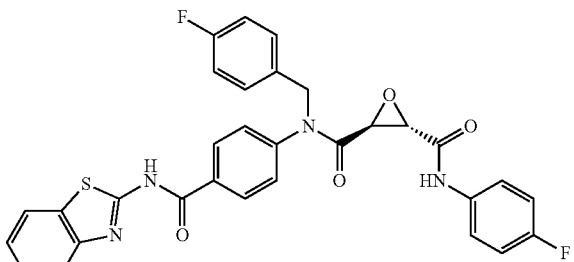

Referring to the preparation method of step 1.7 of Example 1, the 3,4-dimethoxyaniline is replaced with 4-fluoroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.14 g, and the yield is 30%. $[\alpha]_D^{22.3}$=−69.214 (c=1.0, methanol); ¹H-NMR (400 MHz, DMSO-d6, δ ppm) δ 12.89 (s, 1H), 10.47 (s, 1H), 8.16-7.11 (m, 16H), 5.13 (d, 1H, J=16 Hz), 4.96 (d, 1H, J=16 Hz), 3.86 (s, 1H), 3.47 (s, 1H); ESI-MS (m/z): [M+H]⁺ 585.3. m.p. 199.7-200.5° C.

Example 30

Synthesis of (2S,3S)—N²-(4-(benzo[d]thiazol-2-ylcarbamoyl)phenyl)-N³-(3-fluorophenyl)-N²-(4-fluorobenzyl)-2,3-epoxybutanediamide (Compound 30)

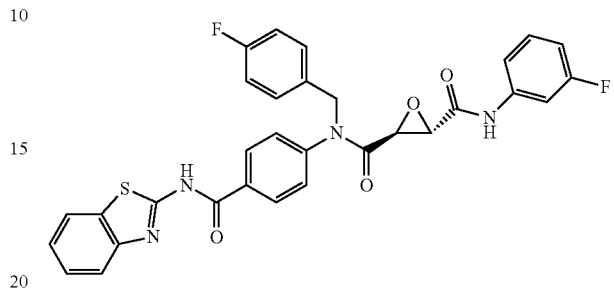

Referring to the preparation method of step 1.7 of Example 1, the 3,4-dimethoxyaniline is replaced with 3-fluoroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.13 g, and the yield is 28%. ¹H-NMR (400 MHz, DMSO-d6, δ ppm) δ 12.90 (s, 1H), 10.63 (s, 1H), 8.15 (d, 2H, J=8.7 Hz), 8.02 (d, 1H, J=7.8 Hz), 7.79 (d, 1H, J=7.3 Hz), 7.54-6.88 (m, 12H), 5.13 (d, 1H, J=15.1 Hz), 4.96 (d, 1H, J=15.1 Hz), 3.89 (s, 1H), 3.48 (s, 1H); ESI-MS (m/z): [M−H]⁻ 583.6. m.p. 202.4-203.1° C.

Example 31

Synthesis of (2S,3S)—N²-(4-(benzo[d]thiazol-2-ylcarbamoyl)phenyl)-N³-(3,4-dichlorophenyl)-N²-(4-fluorobenzyl)-2,3-epoxybutanediamide (Compound 31)

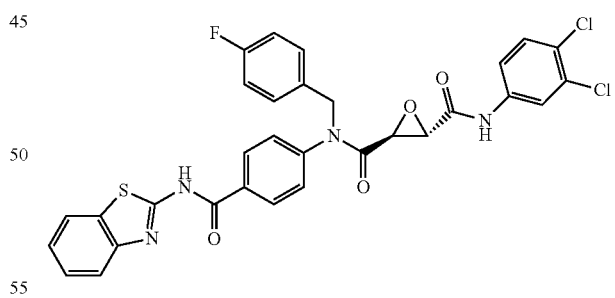

Referring to the preparation method of step 1.7 of Example 1, the 3,4-dimethoxyaniline is replaced with 3,4-dichloroaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.04 g, and the yield is 8%. ¹H-NMR (400 MHz, DMSO-d6, δ ppm) δ 12.86 (s, 1H), 10.64 (s, 1H), 8.16-7.13 (m, 15H), 5.12 (d, 1H, J=15.1 Hz), 4.97 (d, 1H, J=16.0 Hz), 3.86 (s, 1H), 3.50 (s, 1H); ESI-MS (m/z): [M+H]⁺ 635.5. m.p. 218.2-219.1° C.

Example 32

Synthesis of (2S,3S)—N²-(4-(benzo[d]thiazol-2-ylcarbamoyl)phenyl)-N²-(4-fluorobenzyl)-N³-(2-thiazolyl)-2,3-epoxybutanediamide (Compound 32)

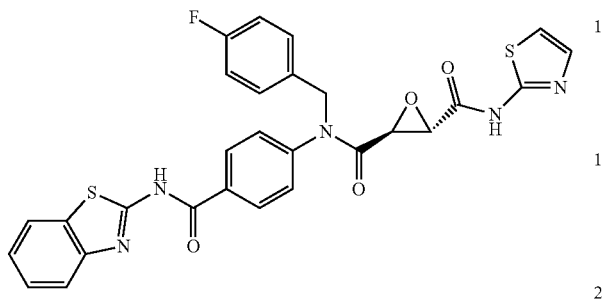

Referring to the preparation method of step 1.7 of Example 1, the 3,4-dimethoxyaniline is replaced with 2-aminothiazole, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.11 g, and the yield is 24%. $^1$H-NMR (400 MHz, DMSO-d6, δ ppm) δ 12.90 (s, 1H), 12.73 (s, 1H), 8.14 (d, 2H, J=8.4 Hz), 8.03 (d, 1H, J=7.3 Hz), 7.79 (d, 1H, J=6.7 Hz), 7.53-7.11 (m, 10H), 5.14 (d, 1H, J=14.8 Hz), 4.95 (d, 1H, J=15.1 Hz), 4.03 (s, 1H), 3.52 (s, 1H); ESI-MS (m/z): [M+H]$^+$ 574.4. m.p. 216.4-217.2° C.

Example 33

Synthesis of (2S,3S)—N²-(4-(benzo[d]thiazol-2-ylcarbamoyl)phenyl)-N²-(4-fluorobenzyl)-N³-(4-ethoxycarbonylthiazol-2-yl)-2,3-epoxybutanediamide (Compound 33)

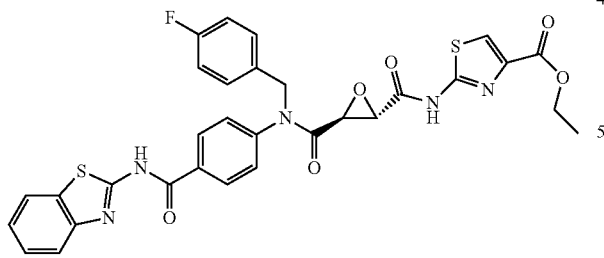

Referring to the preparation method of step 1.7 of Example 1, the 3,4-dimethoxyaniline is replaced with 4-ethoxycarbonylthiazole, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.10 g, and the yield is 20%. $[α]_D^{22.2}$=−59.740 (c=1.0, methanol); $^1$H-NMR (400 MHz, DMSO-d6, δ ppm) δ 13.15 (s, 1H), 12.90 (s, 1H), 8.18-7.17 (m, 13H), 5.16-4.98 (m, 2H), 4.26 (br, 2H), 4.00 (s, 1H), 3.62 (s, 1H), 1.30 (s, 3H); ESI-MS (m/z): [M+H]$^+$ 646.5. m.p. 220.5-221.6° C.

Example 34

Synthesis of (2S,3S)—N²-(4-(benzo[d]thiazol-2-ylcarbamoyl)phenyl)-N²-(4-fluorobenzyl)-N³-(4-methoxycarbonylthiazol-2-yl)-2,3-epoxybutanediamide (Compound 34)

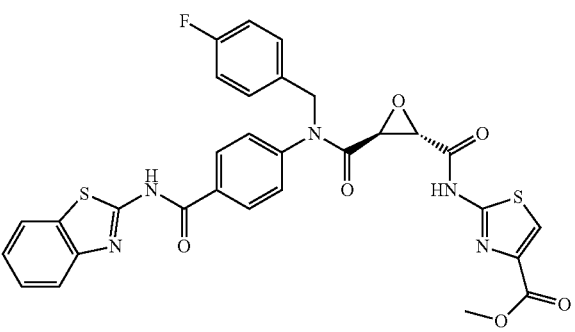 [SMILES: COC(=O)c1csc(NC(=O)[C@H]2O[C@@H]2C(=O)N(Cc2ccc(F)cc2)c2ccc(C(=O)Nc3nc4ccccc4s3)cc2)n1]

Referring to the preparation method of step 1.7 of Example 1, the 3,4-dimethoxyaniline is replaced with 4-methoxycarbonylthiazole, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.01 g, and the yield is 20%. $[α]_D^{22.2}$=−58.776 (c=1.0, methanol); $^1$H-NMR (400 MHz, DMSO-d6, δ ppm) δ 13.10 (s, 1H), 12.93 (s, 1H), 8.13-7.14 (m, 13H), 5.16-4.93 (m, 2H), 3.96 (s, 1H), 3.57 (s, 1H); ESI-MS (m/z): [M−H]$^−$ 630.6. m.p. 196.3-197.1° C.

Example 35

Synthesis of (2S,3S)—N²-(4-(benzo[d]thiazol-2-ylcarbamoyl)phenyl)-N²-(4-fluorobenzyl)-N³-(5-ethoxycarbonylthiazol-2-yl)-2,3-epoxybutanediamide (Compound 35)

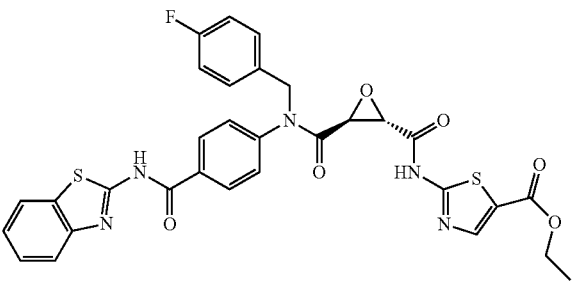 [SMILES: CCOC(=O)c1cnc(NC(=O)[C@H]2O[C@@H]2C(=O)N(Cc2ccc(F)cc2)c2ccc(C(=O)Nc3nc4ccccc4s3)cc2)s1]

Referring to the preparation method of step 1.7 of Example 1, the 3,4-dimethoxyaniline is replaced with 5-ethoxycarbonylthiazole, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.12 g, and the yield is 23%. $[α]_D^{22.1}$=−10.574 (c=1.0, methanol); $^1$H-NMR (400 MHz, DMSO-d6, δ ppm) δ 13.12 (s, 1H), 12.87 (s, 1H), 8.13-7.14 (m, 13H), 5.12-4.92 (m, 2H), 4.15-4.13 (m, 2H), 4.02 (s, 1H), 3.35 (s, 1H), 1.20-1.16 (m, 3H); ESI-MS (m/z): [M−H]$^−$ 644.6. m.p. 218.6-219.2° C.

Example 36

Synthesis of (2S,3S)—N²-(4-(benzo[d]thiazol-2-ylcarbamoyl)phenyl)-N²-(4-fluorobenzyl)-N³-(5-methoxycarbonylthiazol-2-yl)-2,3-epoxybutanediamide (Compound 36)

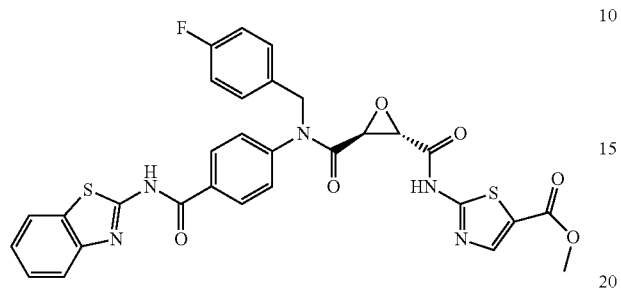

Referring to the preparation method of step 1.7 of Example 1, the 3,4-dimethoxyaniline is replaced with 5-methoxycarbonylthiazole, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.10 g, and the yield is 20%. $[\alpha]_D^{22.2}$=−17.451 (c=1.0, methanol); ¹H-NMR (400 MHz, DMSO-d6, δ ppm) δ 13.15 (s, 1H), 12.87 (s, 1H), 8.15-7.14 (m, 13H), 5.12-4.92 (m, 2H), 4.03 (s, 1H), 3.55 (s, 1H); ESI-MS (m/z): [M+H]⁺ 632.5. m.p. 219.8-220.2° C.

Example 37

Synthesis of (2S,3S)—N²-(4-(benzo[d]thiazol-2-ylcarbamoyl)phenyl)-N³-(2-methoxyphenyl)-N²-(4-fluorobenzyl)-2,3-epoxybutanediamide (Compound 37)

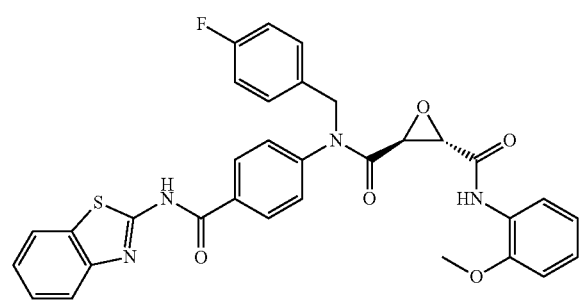 [SMILES: COc1ccccc1NC(=O)[C@H]1O[C@@H]1C(=O)N(Cc1ccc(F)cc1)c1ccc(C(=O)Nc2nc3ccccc3s2)cc1]

Referring to the preparation method of step 1.7 of Example 1, the 3,4-dimethoxyaniline is replaced with 2-methoxyaniline, and the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)(4-fluorobenzyl)carbamoyl)oxirane-2-carboxylic acid to give a white solid of 0.02 g, and the yield is 4%. $[\alpha]_D^{21.6}$=−65.685 (c=1.0, methanol); ¹H-NMR (400 MHz, DMSO-d6, δ ppm) δ 12.87 (s, 1H), 9.63 (s, 1H), 8.11-7.01 (m, 16H), 5.10-4.87 (m, 2H), 4.06 (s, 1H), 3.81 (s, 3H), 3.41 (s, 1H); ESI-MS (m/z): [M+H]⁺ 597.3. m.p. 189.2-190.0° C.

Example 38

Synthesis of (2S,3S)-3-((4-(benzo[d]thiazol-2-ylcarbamoyl)phenyl)(benzyl)carbamoyl)oxirane-2-carboxylic acid (Compound 38)

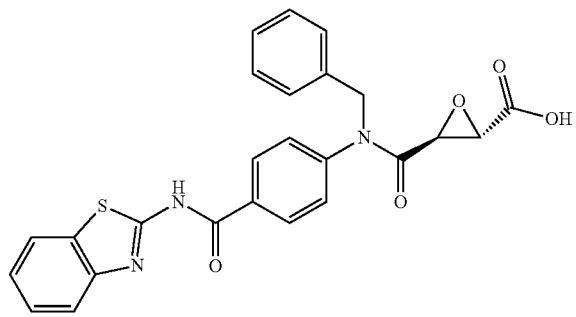 [SMILES: O=C(Nc1nc2ccccc2s1)c1ccc(N(Cc2ccccc2)C(=O)[C@H]2O[C@@H]2C(=O)O)cc1]

Step 38.1 Synthesis of the Intermediate N-(benzo[d]thiazol-2-yl)-4-(benzylamino)benzamide Referring to the method of step 16.3 of Example 16, the fluorobenzaldehyde is replaced with benzaldehyde to give 0.88 g of white solid, and the yield is 67%.

Step 38.2 Synthesis of the Intermediate (2S,3S)-3-((4-(benzo[d]thiazol-2-ylcarbamoyl)phenyl)benzylcarbamoyl)oxirane-2-carboxylic acid ethyl ester Referring to the method of step 16.4 of Example 16, N-(benzo[d]thiazol-2-yl)-4-benzylaminobenzamide is used as the starting material to give 1.2 g of crude brown solid, which is used directly in the next step.

Step 38.3 Synthesis of (2S,3S)-3-((4-(benzo[d]thiazol-2-ylcarbamoyl)phenyl)benzylcarbamoyl)oxirane-2-carboxylic acid Referring to the method of step 16.5 of Example 16, (2S,3S)-3-((4-(benzo[d]thiazol-2-ylcarbamoyl)phenyl)benzylcarbamoyl)oxirane-2-carboxylic acid ester is used as the starting material to give 1.03 g of light pink solid, and the yield is 82%. $[\alpha]_D^{22.8}$=−78.804; ¹H-NMR (400 MHz, DMSO-d6, δ ppm) δ 13.40 (s, 1H), 12.96 (s, 1H), 8.16 (d, 2H, J=8.4 Hz), 8.03 (d, 1H, J=7.9 Hz), 7.79 (d, 1H, J=7.8 Hz), 7.53-7.45 (m, 3H), 7.36-7.22 (m, 6H), 5.08-5.00 (m, 2H), 3.70 (d, 1H, J=1.7 Hz), 3.41 (s, 1H); ESI-MS (m/z): [M−H]⁻ 472.5. m.p. 198.6-199.3° C.

Example 39

Synthesis of (2S,3S)—N²-(4-(benzo[d]thiazol-2-ylcarbamoyl)phenyl)-N²-benzyl-N³-(3,4-dimethoxyphenyl)-2,3-epoxybutanediamide (Compound 39)

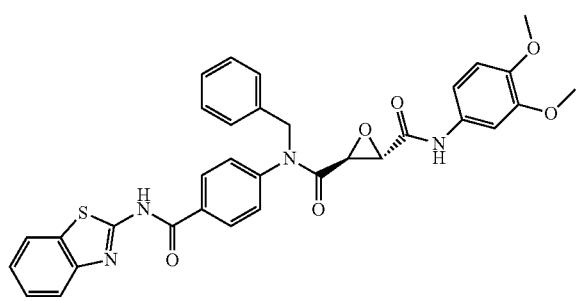 [SMILES: COc1ccc(NC(=O)[C@H]2O[C@@H]2C(=O)N(Cc2ccccc2)c2ccc(C(=O)Nc3nc4ccccc4s3)cc2)cc1OC]

Referring to the preparation method of step 1.7 of Example 1, the (2S,3S)-3-(benzyl(phenyl)carbamoyl)oxirane-2-carboxylic acid is replaced with (2S,3S)-3-((4-(benzo[d]thiazol-2-ylcarbamoyl)phenyl)benzylcarbamoyl) oxirane-2-carboxylic acid to give a white solid of 0.28 g, and the yield is 42%. ¹H-NMR (400 MHz, DMSO-d6, δ ppm) δ 12.89 (s, 1H), 10.30 (s, 1H), 8.14 (d, 2H, J=8.4 Hz), 8.02 (d, 1H, J=7.6 Hz), 7.78 (d, 1H, J=7.5 Hz), 7.55-7.19 (m, 10H), 7.03 (d, 1H, J=8.4 Hz), 6.84 (d, 1H, J=8.6 Hz), 5.16 (d, 1H, J=15.4 Hz), 4.97 (d, 1H, J=15.4 Hz), 3.84 (s, 1H), 3.66 (d, 6H, J=15.1 Hz), 3.47 (s, 1H); ESI-MS (m/z): [M+H]⁺ 609.5. m.p. 224.5-226.0° C.

Example 40

Synthesis of (2S,3S)—N²-(4-(benzo[d]thiazol-2-ylcarbamoyl)phenyl)-N²-benzyl-N³-(3,4-dichlorophenyl)-2,3-epoxybutanediamide (Compound 40)

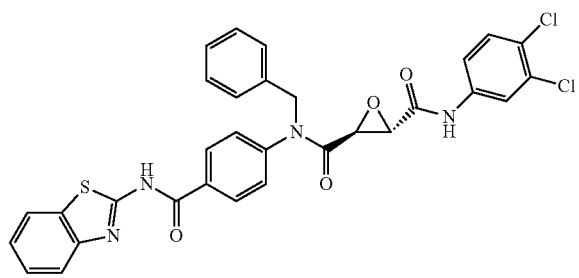 [SMILES: O=C(Nc1nc2ccccc2s1)c1ccc(N(Cc2ccccc2)C(=O)[C@H]2O[C@@H]2C(=O)Nc2ccc(Cl)c(Cl)c2)cc1]

Referring to the preparation method of step 1.7 of Example 1, the 3,4-dimethoxyaniline is replaced with 3,4-dichloroaniline, the (2S,3S)-3-(benzyl(phenyl)carbamoyl) oxirane-2-carboxylic acid is replaced with (2S,3S)-3-((4-(benzo[d]thiazol-2-ylcarbamoyl)phenyl)benzylcarbamoyl) oxirane-2-carboxylic acid to give a white solid of 0.18 g, and the yield is 26%. ¹H-NMR (400 MHz, DMSO-d6, δ ppm) δ 12.90 (s, 1H), 10.68 (s, 1H), 8.14 (d, 2H, J=8.4 Hz), 8.02 (d, 1H, J=7.9 Hz), 7.88 (br, 1H), 7.78 (d, 1H, J=7.8 Hz), 7.54 (d, 3H, J=8.4 Hz), 7.49-7.23 (m, 8H), 5.16 (d, 1H, J=15.1 Hz), 4.98 (d, 1H, J=15.1 Hz), 3.88 (s, 1H), 3.52 (s, 1H); ESI-MS (m/z): [M+H]⁺ 617.6. m.p. 217.6-218.3° C.

Example 41

Synthesis of (2S,3S)—N²-(4-(benzo[d]thiazol-2-ylcarbamoyl)phenyl)-N²-benzyl-N³-(4-methoxycarbonylthiazol-2-yl)-2,3-epoxybutanediamide (Compound 41)

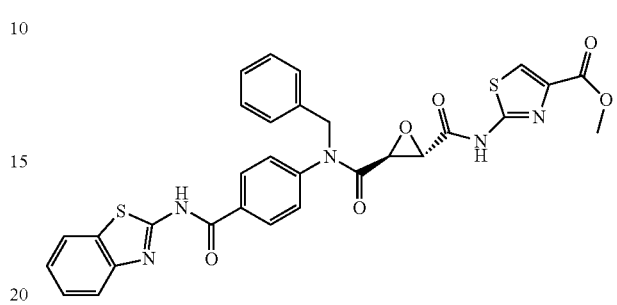

Referring to the preparation method of step 1.7 of Example 1, the 3,4-dimethoxyaniline is replaced with 4-methoxycarbonylthiazole, the (2S,3S)-3-(benzyl(phenyl) carbamoyl)oxirane-2-carboxylic acid is replaced with (2S,3S)-3-((4-(benzo[d]thiazol-2-ylcarbamoyl)phenyl)benzylcarbamoyl)oxirane-2-carboxylic acid to give a white solid of 0.17 g, and the yield is 25%. [α]_D^{21.8}=−51.349 (c=1.0, methanol); ¹H-NMR (400 MHz, DMSO-d6, ppm) δ 13.10 (s, 1H), 12.90 (s, 1H), 8.12-7.23 (m, 14H), 5.15 (d, 1H, J=15.1 Hz), 4.98 (d, 1H, J=15.1 Hz), 3.97 (s, 1H), 3.81 (s, 3H), 3.58 (s, 1H); ESI-MS (m/z): [M+H]⁺ 614.4. m.p. 223.5-224.3° C.

Example 42

Synthesis of (2S,3S)—N²-(4-(benzo[d]thiazol-2-ylcarbamoyl)phenyl)-N²-benzyl-N³-(5-methoxycarbonylthiazol-2-yl)-2,3-epoxybutanediamide (Compound 42)

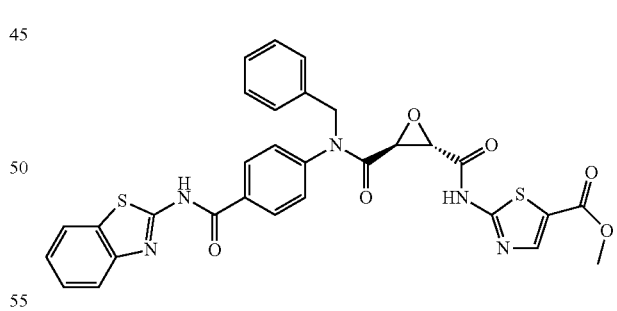

Referring to the preparation method of step 1.7 of Example 1, the 3,4-dimethoxyaniline is replaced with 5-methoxycarbonylthiazole, the (2S,3S)-3-(benzyl(phenyl) carbamoyl)oxirane-2-carboxylic acid is replaced with (2S,3S)-3-((4-(benzo[d]thiazol-2-ylcarbamoyl)phenyl)benzylcarbamoyl)oxirane-2-carboxylic acid to give a white solid of 0.11 g, and the yield is 16%. ¹H-NMR (400 MHz, DMSO-d6, δ ppm) δ 13.16 (s, 1H), 12.86 (s, 1H), 8.12-7.23 (m, 14H), 5.15 (d, 1H, J=15.1 Hz), 4.97 (d, 1H, J=15.1 Hz), 4.04 (s, 1H), 3.67 (s, 3H), 3.57 (s, 1H); ESI-MS (m/z): [M+H]⁺. m.p. 220.1-221.1° C.

Example 43

Synthesis of Racemates of Example 14

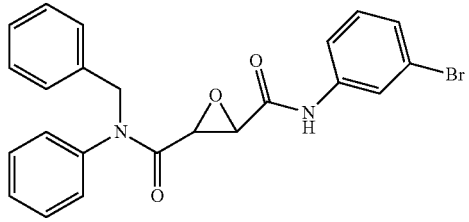 [SMILES: O=C(Nc1cccc(Br)c1)C1OC1C(=O)N(Cc1ccccc1)c1ccccc1]

Step 43.1 Synthesis of 2,3-epoxybutanedioic acid diethyl ester

At room temperature, the 2,3-epoxybutanedioic acid (1 g, 7.6 mmol) is added to a 2 L three-necked flask containing 40 ml of ethanol solution and suspended therein. The upper opening of the flask is equipped with a condenser, a drying tube and a constant pressure dropping funnel. The concentrated sulfuric acid (0.18 ml, 3.04 mmol) is added dropwise with stirring. After addition, the solution is refluxed at 70° C. for 6 hours. After completion of the reaction, the reaction solution is concentrated, and then diluted with 20 ml ice water, and extracted with ethyl acetate (20 ml*3). The organic phase is washed with saturated $NaHCO_3$ (20 ml*2), then with saturated brine (60 ml*2), and dried with $NaSO_4$. Suction filtered, the filtrate is concentrated to give a yellow oily substance. After column chromatography, gradient elution: the columns are rinsed by petroleum ether, petroleum ether/ethyl acetate=20:1, giving a colorless oily substance 2,3-epoxybutanedioic acid diethyl ester, 1.51 g in total, and the yield is 70%.

Step 43.2 Synthesis of 2,3-epoxybutanedioic acid monoethyl ester

Referring to the preparation method of step 1.4 of Example 1, the (2S,3S)-2,3-epoxybutanedioic acid diethyl ester is replaced with 2,3-epoxybutanedioic acid diethyl ester to give a light pink oily substance of 0.89 g, and the yield is 81%.

Step 43.3 Synthesis of 3-(benzyl(phenyl)carbamoyl)-2,3-oxirane-2-carboxylic acid ethyl ester Referring to the preparation method of step 1.5 of Example 1, the (2S,3S)-2,3-epoxybutanedioic acid monoethyl ester is replaced with 2,3-epoxybutanedioic acid monoethyl ester to give a white floc pure product of 12.12 g, and the yield is 80%.

Step 43.4 3-(benzyl(phenyl)carbamoyl)-2,3-oxirane-2-carboxylic acid

Referring to the preparation method of step 1.6 of Example 1, (2S,3S)-3-(benzyl(phenyl)carbamoyl)oxirane-2-carboxylic acid ethyl ester is replaced with 3-(benzyl)(phenyl)carbamoyl)-2,3-oxirane-2-carboxylic acid ethyl ester to give a white solid of 1.00 g, and the yield is 87%.

Step 43.5 Synthesis of $N^2$-benzyl-$N^2$-phenyl-$N^3$-(3-bromophenyl)-2,3-epoxybutanediamide (Compound 43)

Referring to the preparation method of step 1.7 of Example 1, the (2S,3S)-3-(benzyl(phenyl)carbamoyl)oxirane-2-carboxylic acid is replaced with 3-(benzyl)(phenyl)carbamoyl)-2,3-oxirane-2-carboxylic acid to give a white solid of 0.40 g, and the yield is 89%. $^1$H-NMR (400 MHz, DMSO-d6, δ ppm) δ 10.59 (s, 1H), 7.85 (s, 1H), 7.85-7.19 (m, 13H), 5.09 (d, 1H, J=14.3 Hz), 4.86 (d, 1H, J=14.3 Hz), 3.84 (d, 1H, J=1.4 Hz), 3.33 (d, 1H, J=1.4 Hz); ESI-MS (m/z): [M+H]$^+$ 451.5.

Example 44

Activity Against Small RNA Virus of the Compounds of the Invention in In Vitro Model Test item: Activity screening of the compounds for anti-enterovirus EV71

Test principle: Vero cells are used as viral host. The inhibition of the compound of the invention on the degree of cytopathic effect of Vero cells caused by enterovirus virus EV71 is determined.

Test Materials and Methods

1. Virus strain: enterovirus EV71 (BrCr, American Type Culture Collection, ATCC)
2. Sample treatment: the compounds of the present invention are dissolved in DMSO or diluent to prepare stock solution which is stored at −20° C. The stock solution is formulated to suitable incipient concentration with culture solution immediately before use, and then 3-fold diluted with the culture solution, 8 degrees of dilution each.
3. Positive control drug: Pirodavir (LGM Pharma), which is a broad-spectrum anti-viral inhibitor.
4. Test Method: Vero cells are seeded into a 96-well culture plate, at 5% $CO_2$, and cultured at 37° C. for 16 hours. The Vero cells are added with different dilutions of drugs, and the degree of cytopathic effect (CPE) in each group is observed. The half toxic concentration ($TC_{50}$) of each sample for Vero cells is calculated. Vero cells are added with 100TCID$_{50}$ enterovirus EV71 respectively, and the virus solution is discarded after adsorption at 37° C. for 1 hour, and then drugs with various degrees of dilution are added respectively. Virus control and cell control are set and incubated at 37° C. The degree of cytopathic effect (CPE) in each group is observed when the degree of cytopathic effect (CPE) of virus control group reaches 4+. The half inhibitory concentration ($IC_{50}$) of each sample for enterovirus EV71 are calculated. Selectivity Index (SI) is calculated according to the following equation: SI=$TC_{50}$/$IC_{50}$.

Activity screening data of the positive control drug and the compounds 1-42 in Examples are shown in Table 1-1:

TABLE 1-1

Activity screening data of the compounds

| Sample No. | $TC_{50}$ (μg/ml) | EV71 (BrCr strain) $IC_{50}$ (μg/ml) | SI |
|---|---|---|---|
| 1 | 10.68 | >2.47 | — |
| 2 | 10.68 | 2.47 | 4.32 |
| 3 | 5.14 | 2.47 | 2.08 |
| 4 | 7.41 | 2.47 | 3.00 |
| 5 | 10.68 | 2.47 | 4.32 |

TABLE 1-1-continued

Activity screening data of the compounds

| Sample No. | TC$_{50}$ (μg/ml) | EV71 (BrCr strain) IC$_{50}$ (μg/ml) | SI |
|---|---|---|---|
| 6 | 4.28 | 0.82 | 5.22 |
| 7 | 4.28 | 0.27 | 15.85 |
| 8 | 4.28 | 0.27 | 15.85 |
| 9 | 4.28 | 0.82 | 5.22 |
| 10 | 1.43 | 0.15 | 9.53 |
| 11 | 1.43 | 0.15 | 9.53 |
| 12 | 10.68 | 0.23 | 46.43 |
| 13 | 1.19 | >0.27 | — |
| 14 | 12.83 | 1.43 | 8.97 |
| 15 | 1.43 | 0.47 | 3.04 |
| 16 | 17.25 | >2.47 | — |
| 17 | 115.47 | 38.49 | 3.00 |
| 18 | 1.43 | >0.82 | — |
| 19 | 1.43 | >0.82 | — |
| 20 | 13.74 | >2.47 | — |
| 21 | 1.19 | >0.27 | — |
| 22 | 1.19 | >0.27 | — |
| 23 | 1.43 | >0.82 | — |
| 24 | 1.43 | >0.82 | — |
| 25 | 0.82 | >0.27 | — |
| 26 | 1.43 | >0.82 | — |
| 27 | 0.82 | >0.27 | — |
| 28 | 0.82 | >0.27 | — |
| 29 | 1.43 | >0.82 | — |
| 30 | 1.43 | 0.36 | 3.97 |
| 31 | 1.43 | >0.82 | — |
| 32 | 1.19 | >0.27 | — |
| 33 | 1.19 | >0.27 | — |
| 34 | 1.43 | >0.82 | — |
| 35 | 4.28 | >2.47 | — |
| 36 | 3.56 | >0.82 | — |
| 37 | 0.82 | >0.27 | — |
| 38 | 115.47 | >22.22 | — |
| 39 | 32.05 | 4.28 | 7.49 |
| 40 | 1.43 | >0.82 | — |
| 41 | 1.43 | >0.82 | — |
| 42 | 4.28 | >0.82 | — |
| Pirodavir (control drug) | 4.81 | 0.13 | 4.81 |

What is claimed is:

1. A compound of formula I,

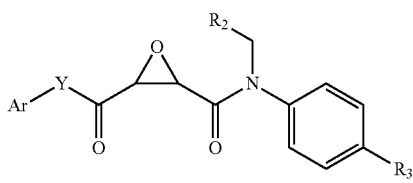

I wherein:
Y is independently —O—, —S—, —C(R$_4$)$_2$—, —N(R$_4$)— or hydroxy, wherein when Y is hydroxy, Ar is absent;
R$_4$ is independently hydrogen or C$_{1-6}$ alkyl;
Ar is independently cycloalkyl, heterocycloalkyl, aryl or heteroaryl, which is optionally and independently mono- or poly-substituted by 1, 2, 3, 4 or 5 R$_1$;
R$_1$ is independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl or nitro;
R$_2$ is independently hydrogen, halogen, aryl or heteroaryl, wherein said aryl or heteroaryl is optionally and independently mono- or poly-substituted by 1, 2, 3, 4 or 5 substituents, and the substituents are independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl or nitro;
R$_3$ is independently hydrogen, halogen, alkyl, alkenyl, alkynyl, alkoxy, hydroxy, cyano, amino, alkylamino, dialkylamino, cyanoalkyl, hydroxyalkyl, haloalkyl, haloalkoxy, alkylthio, cycloalkyl, heterocycloalkyl, alkoxycarbonyl, nitro or a group of formula

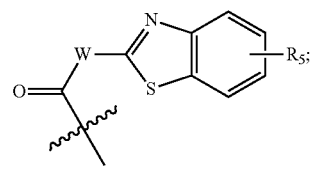

R$_5$ is independently hydrogen or C$_{1-6}$ alkyl;
W is independently —C(R$_6$)$_2$—, —NR$_6$—, —O— or —S—; and
R$_6$ is independently hydrogen or C$_{1-6}$ alkyl,
or optical isomer, pharmaceutically acceptable salt, solvate or hydrate thereof.

2. The compound of formula I according to claim 1, or optical isomer, pharmaceutically acceptable salt, solvate or hydrate thereof, wherein Y is —N(R$_4$)— or hydroxy, and wherein R$_4$ is independently hydrogen or C$_{1-6}$ alkyl.

3. The compound of formula I according to claim 1, or optical isomer, pharmaceutically acceptable salt, solvate or hydrate, wherein Ar is aryl or heteroaryl, which is optionally and independently mono- or poly-substituted by 1, 2 or 3 R$_1$.

4. The compound of formula I according to claim 1, or optical isomer, pharmaceutically acceptable salt, solvate or hydrate thereof, wherein R$_1$ is independently hydrogen, halogen, alkyl, alkoxy, hydroxy, cyano, amino, alkylamino, dialkylamino, hydroxyalkyl, haloalkyl, haloalkoxy, alkylthio, alkoxycarbonyl or nitro.

5. The compound of formula I according to claim 1, or optical isomer, pharmaceutically acceptable salt, solvate or hydrate thereof, wherein R$_2$ is aryl or heteroaryl, which is optionally and independently mono- or poly-substituted by 1, 2 or 3 substituents, and the substituents are independently hydrogen, halogen, alkyl, alkoxy, hydroxy, amino, alkylamino, dialkylamino, haloalkyl, haloalkoxy or alkylthio, preferably hydrogen, halogen, alkyl, alkoxy, hydroxy or amino, more preferably hydrogen or halogen.

6. The compound of formula I according to claim 1, or optical isomer, pharmaceutically acceptable salt, solvate or hydrate thereof, wherein R$_3$ is independently hydrogen, halogen, alkyl, alkoxy, hydroxy, cyano, amino, alkylamino, dialkylamino, alkylthio or a group of formula

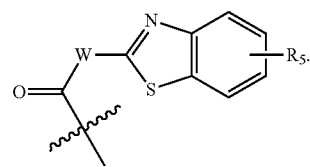

7. The compound of formula I according to claim 1, or optical isomer, pharmaceutically acceptable salt, solvate or hydrate thereof, wherein $R_3$ is independently hydrogen or a group of formula

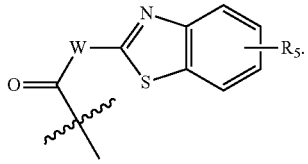

8. The compound of formula I according to claim 1, or optical isomer, pharmaceutically acceptable salt, solvate or hydrate thereof, wherein W is —N($R_6$)—, wherein $R_6$ is independently hydrogen or $C_{1-6}$ alkyl, preferably hydrogen.

9. The compound of formula I according to claim 1, or optical isomer, pharmaceutically acceptable salt, solvate or hydrate thereof, selected from the group consisting of:
- (2S,3S)—$N^2$-benzyl-$N^2$-phenyl-$N^3$-(3,4-dimethoxyphenyl)-2,3-epoxybutanediamide (Compound 1);
- (2S,3S)—$N^2$-benzyl-$N^2$-phenyl-$N^3$-(2-thiazolyl)-2,3-epoxybutanediamide (Compound 2);
- (2S,3S)—$N^2$-benzyl-$N^2$-phenyl-$N^3$-(3,4-dichlorophenyl)-2,3-epoxybutanediamide (Compound 3);
- (2S,3S)—$N^2$-benzyl-$N^2$-phenyl-$N^3$-(3-fluorophenyl)-2,3-epoxybutanediamide (Compound 4);
- (2S,3S)—$N^2$-benzyl-$N^2$-phenyl-$N^3$-(4-fluorophenyl)-2,3-epoxybutanediamide (Compound 5);
- (2S,3S)—$N^2$-benzyl-$N^2$-phenyl-$N^3$-(2-fluorophenyl)-2,3-epoxybutanediamide (Compound 6);
- (2S,3S)—$N^2$-benzyl-$N^2$-phenyl-$N^3$-(3-methoxyphenyl)-2,3-epoxybutanediamide (Compound 7);
- (2S,3S)—$N^2$-benzyl-$N^2$-phenyl-$N^3$-(3-chlorophenyl)-2,3-epoxybutanediamide (Compound 8);
- (2S,3S)—$N^2$-benzyl-$N^2$-phenyl-$N^3$-(4-nitrophenyl)-2,3-epoxybutanediamide (Compound 9);
- (2S,3S)—$N^2$-benzyl-$N^2$-phenyl-$N^3$-(2,3-dichlorophenyl)-2,3-epoxybutanediamide (Compound 10);
- (2S,3S)—$N^2$-benzyl-$N^2$-phenyl-$N^3$-(2-chlorophenyl)-2,3-epoxybutanediamide (Compound 11);
- (2S,3S)—$N^2$-benzyl-$N^2$-phenyl-$N^3$-(4-chlorophenyl)-2,3-epoxybutanediamide (Compound 12);
- (2S,3S)—$N^2$-benzyl-$N^2$-phenyl-$N^3$-(2-methyl-3-chlorophenyl)-2,3-epoxybutanediamide (Compound 13)
- (2S,3S)—$N^2$-benzyl-$N^2$-phenyl-$N^3$-(3-bromophenyl)-2,3-epoxybutanediamide (Compound 14);
- (2S,3S)—$N^2$-benzyl-$N^2$-phenyl-$N^3$-(2-bromophenyl)-2,3-epoxybutanediamide (Compound 15);
- (2S,3S)-3-((4-(benzo[d]thiazol-2-ylcarbamoyl)phenyl)(4-fluorobenzyl)carbamoyl) oxirane-2-carboxylic acid (Compound 16);
- (2S,3S)—$N^2$-(4-(benzo[d]thiazol-2-ylcarbamoyl)phenyl)-$N^3$-(3,4-dimethoxyphenyl)-$N^2$-(4-fluorobenzyl)-2,3-epoxybutanediamide (Compound 17);
- (2S,3S)—$N^2$-(4-(benzo[d]thiazol-2-ylcarbamoyl)phenyl)-$N^3$-(3-bromophenyl)-$N^2$-(4-fluorobenzyl)-2,3-epoxybutanediamide (Compound 18);
- (2S,3S)—$N^2$-(4-(benzo[d]thiazol-2-ylcarbamoyl)phenyl)-$N^3$-(4-chlorophenyl)-$N^2$-(4-fluorobenzyl)-2,3-epoxybutanediamide (Compound 19);
- (2S,3S)—$N^2$-(4-(benzo[d]thiazol-2-ylcarbamoyl)phenyl)-$N^3$-(4-methoxyphenyl)-$N^2$-(4-fluorobenzyl)-2,3-epoxybutanediamide (Compound 20);
- (2S,3S)—$N^2$-(4-(benzo[d]thiazol-2-ylcarbamoyl)phenyl)-$N^3$-(3-methoxyphenyl)-$N^2$-(4-fluorobenzyl)-2,3-epoxybutanediamide (Compound 21);
- (2S,3S)—$N^2$-(4-(benzo[d]thiazol-2-ylcarbamoyl)phenyl)-$N^3$-(3,4-difluorophenyl)-$N^2$-(4-fluorobenzyl)-2,3-epoxybutanediamide (Compound 22);
- (2S,3S)—$N^2$-(4-(benzo[d]thiazol-2-ylcarbamoyl)phenyl)-$N^3$-(3-chlorophenyl)-$N^2$-(4-fluorobenzyl)-2,3-epoxybutanediamide (Compound 23);
- (2S,3S)—$N^2$-(4-(benzo[d]thiazol-2-ylcarbamoyl)phenyl)-$N^3$-(4-nitrophenyl)-$N^2$-(4-fluorobenzyl)-2,3-epoxybutanediamide (Compound 24);
- (2S,3S)—$N^2$-(4-(benzo[d]thiazol-2-ylcarbamoyl)phenyl)-$N^3$-(2,3-dichlorophenyl)-$N^2$-(4-fluorobenzyl)-2,3-epoxybutanediamide (Compound 25);
- (2S,3S)—$N^2$-(4-(benzo[d]thiazol-2-ylcarbamoyl)phenyl)-$N^3$-(2,4-dichlorophenyl)-$N^2$-(4-fluorobenzyl)-2,3-epoxybutanediamide (Compound 26);
- (2S,3S)—$N^2$-(4-(benzo[d]thiazol-2-ylcarbamoyl)phenyl)-$N^3$-(2-bromophenyl)-$N^2$-(4-fluorobenzyl)-2,3-epoxybutanediamide (Compound 27);
- (2S,3S)—$N^2$-(4-(benzo[d]thiazol-2-ylcarbamoyl)phenyl)-$N^3$-(2-methyl-3-chlorophenyl)-$N^2$-(4-fluorobenzyl)-2,3-epoxybutanediamide (Compound 28);
- (2S,3S)—$N^2$-(4-(benzo[d]thiazol-2-ylcarbamoyl)phenyl)-$N^3$-(4-fluorophenyl)-$N^2$-(4-fluorobenzyl)-2,3-epoxybutanediamide (Compound 29);
- (2S,3S)—$N^2$-(4-(benzo[d]thiazol-2-ylcarbamoyl)phenyl)-$N^3$-(3-fluorophenyl)-$N^2$-(4-fluorobenzyl)-2,3-epoxybutanediamide (Compound 30);
- (2S,3S)—$N^2$-(4-(benzo[d]thiazol-2-ylcarbamoyl)phenyl)-$N^3$-(3,4-dichlorophenyl)-$N^2$-(4-fluorobenzyl)-2,3-epoxybutanediamide (Compound 31);
- (2S,3S)—$N^2$-(4-(benzo[d]thiazol-2-ylcarbamoyl)phenyl)-$N^2$-(4-fluorobenzyl)-$N^3$-(2-thiazolyl)-2,3-epoxybutanediamide (Compound 32);
- (2S,3S)—$N^2$-(4-(benzo[d]thiazol-2-ylcarbamoyl)phenyl)-$N^2$-(4-fluorobenzyl)-$N^3$-(4-ethoxycarbonylthiazol-2-yl)-2,3-epoxybutanediamide (Compound 33);
- (2S,3S)—$N^2$-(4-(benzo[d]thiazol-2-ylcarbamoyl)phenyl)-$N^2$-(4-fluorobenzyl)-$N^3$-(4-methoxycarbonylthiazol-2-yl)-2,3-epoxybutanediamide (Compound 34);
- (2S,3S)—$N^2$-(4-(benzo[d]thiazol-2-ylcarbamoyl)phenyl)-$N^2$-(4-fluorobenzyl)-$N^3$-(5-ethoxycarbonylthiazol-2-yl)-2,3-epoxybutanediamide (Compound 35);
- (2S,3S)—$N^2$-(4-(benzo[d]thiazol-2-ylcarbamoyl)phenyl)-$N^2$-(4-fluorobenzyl)-$N^3$-(5-methoxycarbonylthiazol-2-yl)-2,3-epoxybutanediamide (Compound 36);
- (2S,3S)—$N^2$-(4-(benzo[d]thiazol-2-ylcarbamoyl)phenyl)-$N^3$-(2-methoxyphenyl)-$N^2$-(4-fluorobenzyl)-2,3-epoxybutanediamide (Compound 37);
- (2S,3S)-3-((4-(benzo[d]thiazol-2-ylcarbamoyl)phenyl)(benzyl)carbamoyl)oxirane-2-carboxylic acid (Compound 38);
- (2S,3S)—$N^2$-(4-(benzo[d]thiazol-2-ylcarbamoyl)phenyl)-$N^2$-benzyl-$N^3$-(3,4-dimethoxy phenyl)-2,3-epoxybutanediamide (Compound 39);
- (2S,3S)—$N^2$-(4-(benzo[d]thiazol-2-ylcarbamoyl)phenyl)-$N^2$-benzyl-$N^3$-(3,4-dichloro phenyl)-2,3-epoxybutanediamide (Compound 40);
- (2S,3S)—$N^2$-(4-(benzo[d]thiazol-2-ylcarbamoyl)phenyl)-$N^2$-benzyl-$N^3$-(4-methoxy carbonylthiazol-2-yl)-2,3-epoxybutanediamide (Compound 41);
- (2S,3S)—$N^2$-(4-(benzo[d]thiazol-2-ylcarbamoyl)phenyl)-$N^2$-benzyl-$N^3$-(5-methoxy carbonylthiazol-2-yl)-2,3-epoxybutanediamide (Compound 42); and $N^2$-benzyl-$N^2$-phenyl-$N^3$-(3-bromophenyl)-2,3-epoxybutanediamide (Compound 43).

10. A pharmaceutical composition, comprising a therapeutically effective amount of the compound of formula I according to claim 1 or optical isomer, pharmaceutically acceptable salt, solvate or hydrate thereof.

11. A method for treating diseases or conditions related to enterovirus 71 infections in a subject, comprising administering a therapeutically effective amount of at least one of the compound of formula I according to claim 1, or optical isomer, pharmaceutically acceptable salt, solvate or hydrate thereof, to the subject in need thereof.

12. The compound of formula I according to claim 1, or optical isomer, pharmaceutically acceptable salt, solvate or hydrate thereof, wherein Y is —N($R_4$)— or hydroxyl, and wherein $R_4$ is hydrogen.

13. The pharmaceutical composition according to claim 10 for the treatment of diseases or conditions related to enterovirus 71 infections.

14. A method for treating diseases or conditions related to enterovirus 71 infections in a subject, comprising administering a therapeutically effective amount of the pharmaceutical composition according to claim 10 to the subject in need thereof.

* * * * *

UNITED STATES PATENT AND TRADEMARK OFFICE
CERTIFICATE OF CORRECTION

PATENT NO. : 9,630,957 B2
APPLICATION NO. : 14/893391
DATED : April 25, 2017
INVENTOR(S) : Li et al.

Page 1 of 1

It is certified that error appears in the above-identified patent and that said Letters Patent is hereby corrected as shown below:

On the Title Page

Missing Item (30) should be added as follows: --Foreign Application Priority Data-- with Foreign Application Date of --May 31, 2013-- and Foreign Application Number of --CN 201310210954.0--.

In the Claims

Column 44,
Line 25, Claim 1, delete "—$NR_6$)—" and insert therein -- —$N(R_6)$ — --.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*